United States Patent
Kristen et al.

(10) Patent No.: US 6,818,715 B1
(45) Date of Patent: Nov. 16, 2004

(54) BISIMIDINO COMPOUNDS AND THE TRANSITIONAL METAL COMPLEXES THEREOF AS WELL AS THE USE THEREOF AS CATALYSTS

(75) Inventors: Marc Oliver Kristen, Limburgerhof (DE); Andrei Gonioukh, Dudenhofen (DE); Dieter Lilge, Limburgerhof (DE); Stephan Lehmann, Ludwigshafen (DE); Benno Bildstein, Innsbruck (AU); Christoph Amort, Rodeneck (IT); Michael Malaun, Wenns (AU)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/049,861

(22) PCT Filed: Aug. 8, 2000

(86) PCT No.: PCT/EP00/07857

§ 371 (c)(1),
(2), (4) Date: Feb. 19, 2002

(87) PCT Pub. No.: WO01/14391

PCT Pub. Date: Mar. 1, 2001

(30) Foreign Application Priority Data

Aug. 20, 1999 (DE) .......................................... 199 39 415

(51) Int. Cl.$^7$ ................................................. C08F 4/06
(52) U.S. Cl. ........................ 526/172; 526/161; 548/566; 548/569; 546/329
(58) Field of Search ................................. 526/134, 108, 526/161, 169, 169.1, 169.2, 172, 348, 346, 341; 502/117; 556/136, 138

(56) References Cited

U.S. PATENT DOCUMENTS

| | | | |
|---|---|---|---|
| 6,281,303 B1 * | 8/2001 | Lavoie et al. | 526/127 |
| 6,461,994 B1 * | 10/2002 | Gibson et al. | 502/155 |
| 6,465,386 B1 * | 10/2002 | Maddox et al. | 502/155 |
| 6,472,341 B1 * | 10/2002 | Kimberly et al. | 502/155 |

FOREIGN PATENT DOCUMENTS

| | | | |
|---|---|---|---|
| WO | WO 91/09882 | 7/1991 | |
| WO | WO 98/27124 A1 * | 6/1998 | C08F/10/00 |
| WO | WO 98/30612 A1 * | 7/1998 | C08F/10/06 |
| WO | WO 99/12981 | 3/1999 | |
| WO | WO 99/12981 A1 * | 3/1999 | C08F/4/70 |
| WO | WO 00/15646 | 3/2000 | |
| WO | WO 00/20427 | 4/2000 | |
| WO | WO 00/50470 | 8/2000 | |

OTHER PUBLICATIONS

Sengupta, S. K.; Pandey, O.P.; Rao, G. P. Sugarcane Pathology 1999, vol. 1, 279–300 (abstract).*

Britovesek et al. "Novel olefin polymerization catalyst based on iron and cobalt" Chem Commun. (1998) pp. 849–850.

Small et al. "Highly active iron and cobalt catalysts for the polymerization of ethylene" J. Am. Chem. Soc. vol. 120 (1998) pge 4049–4050.

Ito et al. "Reaction of ketone enolates with copper bichloride. A synthesis of 1,4–diketones" J. of Am. Chem. Soc. vol. 97 No. 10 (1975) pgs 2912–2914.

Klein et al. "Synthesis and Structure—Activity Relationships of N–Propyl–N–(4–pyridinyl)–1H–indol–1–amine (Bespiridine) and Related Analogs as Potential Therapeutic Agent for Alzheimer's Disease" J. Med. Chem. vol. 39, (1996) pp. 570–581.

Herbst et al. "Studies on the formation of 4–Aminotriazole Derivatives from Acyl Hydrazides"Stetter "Die Katalysierte Addition von Aldehyden an aktivierte Doppelbindungen—Ein neues Syntheseprinzip" Angew. Chem. vol. 88 (1976) pge 695–704.

Stetter et al. "Addition aliphatischer, heterocyclischer und aromatischer Aldehyde an Butenon" Chem Ber. vol. 109 (1976) pp. 3426–3431.

* cited by examiner

Primary Examiner—David W. Wu
Assistant Examiner—Rip A. Lee
(74) Attorney, Agent, or Firm—Keil & Weinkauf

(57) ABSTRACT

Bisimine compounds of the formula (I)

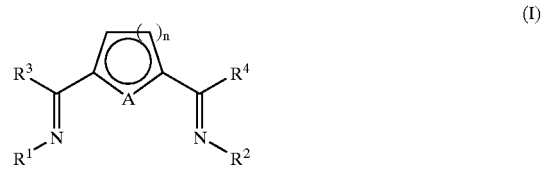

where the symbols are defined in the specification are used to prepare bisimidinato complexes which can be used in the polymerization of unsaturated compounds.

7 Claims, No Drawings

BISIMIDINO COMPOUNDS AND THE TRANSITIONAL METAL COMPLEXES THEREOF AS WELL AS THE USE THEREOF AS CATALYSTS

The present invention relates to bisimidine compounds, a process for their preparation, bisimidinato complexes as catalysts, a process for preparing them and their use in the polymerization of unsaturated compounds.

There is great interest in the development of novel families of catalysts for the polymerization of unsaturated compounds in order to obtain better control over the properties of polyolefins or further novel products.

Use of transition metal compounds as catalytically active substances for the polymerization of unsaturated compounds has been known for a long time. For example, Ziegler-Natta or Phillips catalysts are used commercially for the synthesis of polyolefins. More recently, metallocenes are being used as highly active polymerization catalysts. The metallocenes make it possible to obtain polymers having a narrow molecular weight distribution and copolymers having a uniform comonomer content.

However, metallocene catalysts have disadvantages for industrial use. For example, they are very sensitive to impurities in commercially available monomers, in the process gas and in the solvents used and to hydrolysis. Furthermore, the price of metallocenes having zirconium as central metal is very high.

It has been known for some time that new types of iron and cobalt complexes containing bisimidine ligands are very active as catalysts in the polymerization of unsaturated compounds.

V. C. Gibson et al., Chem. Commun. 1998, 849–850, and M. Brookhart et al., J. Am. Chem. Soc. 1998, 120, 4049–4050, disclose new olefin polymerization catalysts based on Fe(II) and Co(II). These catalysts contain 2,6-bis (imino)pyridyl ligands which are aryl-substituted on the imino nitrogens and display high activities in the polymerization of ethylene. The polyethylene obtained is essentially linear and the molecular weight is strongly dependent on the substituents on the alkyl radical.

WO 99/12981 describes bisimidinato complexes, their synthesis and their use in the polymerization of unsaturated compounds. Numerous complexes having a variety of different radicals are disclosed.

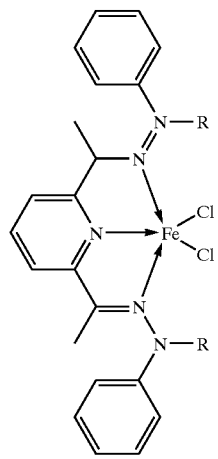

Examples 30 and 31 disclose complexes of the formula A in which R=$CH_3$ and $C_6H_5$. However, the demonstrated activities in the polymerization of ethylene are much too low for industrial applications.

It is an object of the present invention to provide novel complexes containing a metal of groups 7, 8, 9 or 10 of the Periodic Table of the Elements (late transition metal) as central metal which can be used for the polymerization of unsaturated compounds and give branched polymers in the polymerization. This object can be subdivided into the provision of a ligand system for this catalyst and a process for preparing this ligand system and the provision of a process for preparing the corresponding catalyst.

We have found that this object is achieved by compounds of the formula (I)

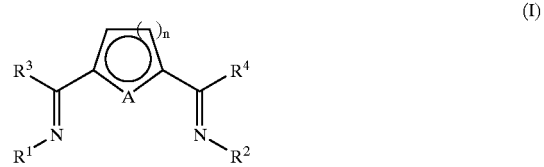

where the symbols have the following meanings:
A is a nonmetal selected from among N, S, O and P,
$R^1$ is a radical of the formula $NR^5R^6$,
$R^2$ is a radical of the formula $NR^5R^6$ or $NR^7R^8$, where $R^5$ and $R^6$ are selected from among alkyl, aryl and cycloalkyl, and
$R^5$ and $R^6$ together with the N atom form a 5-, 6- or 7-membered ring in which one or more of the —CH— or —$CH_2$— groups may be replaced by suitable heteroatom groups and which may be saturated or unsaturated and unsubstituted or substituted or be fused with further carbacyclic or heterocarbacyclic 5- or 6-membered rings which may in turn be saturated or unsaturated and substituted or unsubstituted, and
$R^7$ and $R^8$ are, independently of one another, alkyl, aryl or cycloalkyl radicals, and
$R^3$, $R^4$ are, independently of one another, H or alkyl, aryl or cycloalkyl radicals, and
n is 1 or 2.

The bisimidines of the present invention have at least one nitrogen-nitrogen bond to at least one of the two imine nitrogens as [=N—$NR^5R^6$], where the substituents $R^5$ and $R^6$ together form a cyclic substituent.

These compounds are particularly useful as ligand systems for preparing novel, efficient catalyst systems for the polymerization or copolymerization of unsaturated compounds. These novel ligands are simple to prepare and make it possible to vary the radicals within a wide range. This system is therefore very variable and allows the ligand and complex systems to be tailored to various applications. Use of compounds of the formula (I) as ligand system makes it possible to obtain highly active catalysts for the polymerization of unsaturated compounds.

Above and in the following, alkyl radicals are generally linear or branched $C_1$–$C_{20}$-alkyl radicals, preferably $C_1$–$C_{10}$-alkyl radicals, particularly preferably $C_1$–$C_8$-alkyl radicals. These alkyl radicals can be substituted by heteroatoms. Suitable alkyl radicals are, for example, methyl, i-propyl, t-butyl, trifluoromethyl and trimethylsilyl radicals.

Aryl radicals are generally unsubstituted and substituted $C_6$–$C_{20}$-aryl radicals (the number of carbon atoms refers to the carbon atoms in the aryl radical), preferably $C_6$–$C_{14}$-aryl radicals, which may be unsubstituted or bear one or more substituents; very particularly preference is given to $C_6$–$C_{10}$-aryl radicals, substituted by $C_1$–$C_6$-alkyl radicals, e.g. 4-methylphenyl, 2,6-dimethylphenyl, 2,6-diethylphenyl, 2,6-diisopropylphenyl, 2-tert-butylphenyl, 2,6-di(tert-butyl)phenyl or 2-i-propyl-6-methylphenyl. The aryl radicals can also be substituted by heteroatoms, e.g. by F.

Cycloalkyl radicals are generally $C_5$–$C_8$-cycloalkyl radicals (the number of carbon atoms refers to the carbon atoms in the cycloalkyl ring) which may be unsubstituted or substituted by one or more alkyl or aryl radicals or heteroatoms. Preference is given to $C_5$–$C_6$-cycloalkyl radicals.

In the compounds of the present invention, $R^5$ and $R^6$ together with the N atom form a 5-, 6- or 7-membered ring in which one or more of the —CH— or —CH$_2$— groups may be replaced by suitable heteroatom groups. Suitable heteroatom groups are preferably —N— or —NH— groups. Particular preference is given to from 0 to 3 —CH— or —CH$_2$— groups being replaced by —N— or —NH— groups.

The 5-, 6- or 7-membered ring can be saturated or unsaturated. In the latter case, the ring may be monounsaturated or polyunsaturated. Preference is given to unsaturated 5-membered rings. For the purposes of the present invention, unsaturated rings include, in the case of the 5-membered rings, aromatic rings such as unsubstituted or substituted pyrrole radicals and derivatives thereof, which are particularly preferred.

The 5-, 6- or 7-membered ring may be unsubstituted, substituted or fused with further carbacyclic or heterocarbacyclic 5- or 6-membered rings which may in turn be saturated or unsaturated and substituted or unsubstituted.

For the purposes of the present invention, carbacyclic rings are rings whose skeleton is made up entirely of carbon. In the heterocarbacyclic rings, one or more —CH$_2$— or —CH— groups are replaced by heteroatoms, preferably —NH— or —N— groups. Particular preference is given to carbacyclic rings or heterocarbacyclic rings having a nitrogen atom in the ring system.

Possible substituents in these carbacyclic and heterocarbacyclic 5- or 6-membered rings are the abovementioned alkyl, aryl or cycloalkyl radicals. The rings may bear one or more substituents. Preference is given to from 1 to 3 substituents. Furthermore, the ring systems may be orthofused or orthofused and perifused. The system is preferably orthofused, with particular preference being given to 1 or 2 phenyl radicals being fused onto the central 5- or 6-membered ring, e.g. indole, carbazole and derivatives thereof.

In a particularly preferred embodiment, the ring described by the formula $NR^5R^6$ is 5-membered. Very particular preference is given to an unfused 5-membered ring, in particular a pyrrole radical or a radical derived from pyrrole, in which no, one or more, preferably from 0 to 3, particularly preferably 0 or 2, —CH— groups in the pyrrole ring may be replaced by nitrogen. Examples are the pyrrole system and the triazole system. Particular preference is given to pyrrole radicals or radicals derived from pyrrole which are substituted in the 2 and 5 positions by: $C_1$–$C_6$-alkyl groups which may be linear, branched and substituted by heteroatoms, or electron-withdrawing radicals such as halogen, nitro, sulfonate or trihalomethyl.

Suitable sulfonate radicals are, in particular, $SO_3R^*$, $SO_3Si(R^*)_3$ and $SO_3$—$(HN(R^*)_3)^+$. Among these, $SO_3Me$, $SO_3SiMe_3$ and $SO_3$—$(HNEt_3)$+ are particularly useful. Among the trihalomethyl radicals, trifluoromethyl, trichloromethyl and tribromomethyl, especially trifluoromethyl are particularly useful. Particularly useful ortho substituents are halogen radicals such as fluorine, chlorine, bromine or iodine. Preference is given to using chlorine or bromine as ortho substituents. Furthermore, the respective ortho positions are preferably occupied by identical radicals. Aryl groups may be unsubstituted or substituted in turn by $C_1$–$C_6$-alkyl groups which may be heteroatom-substituted. Preferred substituents in the 2 and 5 positions of the pyrrole ring or a derivative thereof, preferably triazole, are methyl-, i-propyl-, t-butyl- and phenyl-substituted aryl radicals, as defined above.

According to the present invention, $R^3$ and $R^4$ in the formula (I) can be, independently of one another, H or alkyl, aryl or cycloalkyl radicals, with preferred radicals having been defined above. $R^3$ and $R^4$ are very particularly preferably, independently of one another, H or $CH_3$.

According to the present invention, $R^*$ can be H, alkyl, aryl or cycloalkyl, with preferred radicals having been defined above. $R^*$ is very particularly preferably $CH_3$ or H.

Preference is given to using compounds of the formula (I) in which A=N or S. A is particularly preferably N. The central ring is preferably a 6-membered ring, i.e. n is preferably 2. Thus, pyridinebisimidine systems are very particularly preferred.

Particular preference is given to compounds of the formulae (Ia) to (Id):

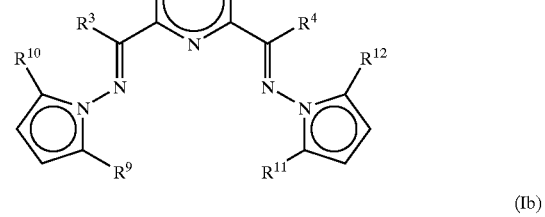

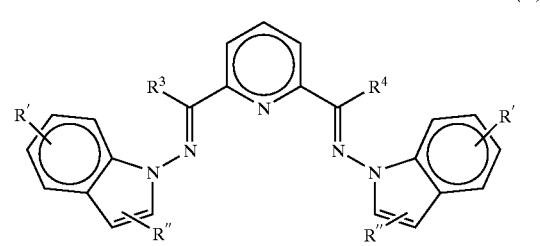

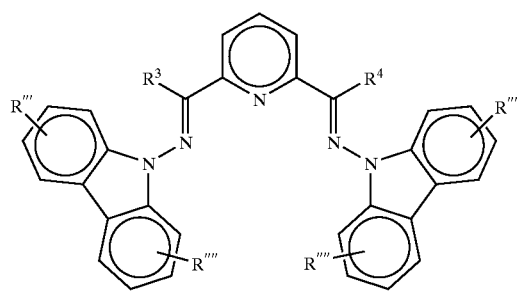

(Ic)

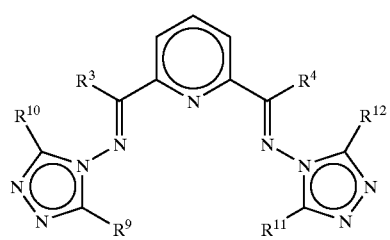

(Id)

where $R^3$, $R^4$, $R^9$ and $R^{10}$ are, independently of one another, $C_1$–$C_{20}$-alkyl radicals which may be linear or branched, preferably $C_1$–$C_{10}$-alkyl radicals, particularly preferably $C_1$–$C_6$-alkyl radicals. These alkyl radicals may be heteroatom-substituted. Suitable alkyl radicals are, for example, methyl, i-propyl, t-butyl, trifluoromethyl and trimethylsilyl radicals. The radicals R', R", R'" and R"" are H or alkyl, aryl or cycloalkyl radicals, as defined above.

The novel compounds of the formula (I)

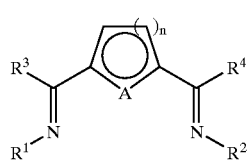

(I)

where $R^1$ is a radical of the formula $NR^5R^6$, $R^2$ is a radical of the formula $NR^5R^6$, $NR^7R^8$ or an alkyl, aryl or cycloalkyl radical, and the other symbols are as defined above, are generally prepared by condensation of the corresponding amino compounds with the corresponding diketo compounds, e.g. 2,5-diformylthiophene or 2,6-diacetylpyridine. They are very readily synthesized and it is possible to synthesize a large number of different compounds of the formula (I) in good yields.

The preferred method of preparation is dependent on the desired compound of the formula (I). In the following, a description is given of preferred embodiments for preparing symmetrical compounds of the formula I in which $R^1$=$R^2$=$NR^5R^6$ and unsymmetrical compounds of the formula I in which $R^1$≠$R^2$ and $R^2$ is a radical of the formula $NR^5R^6$ which is different from $R^1$ which is a radical of the formula $NR^7R^8$ or an alkyl, aryl or cycloalkyl radical.

In a preferred embodiment, symmetrical compounds of the formula (I) in which $R^1$=$R^2$ are prepared by reacting compounds of the formula (II)

(II)

where $R^5$ and $R^6$ are as defined above, with diketo compounds of the formula (III),

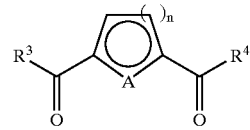

(III)

where $R^3$, $R^4$ are, independently of one another H or alkyl, aryl or cycloalkyl radicals, and A is S, N, O or P, and n is 1 or 2.

The process is carried out in one step under acidic reaction conditions, preferably with addition of a mineral acid or an organic acid, particularly preferably formic acid, in alcoholic solvents, preferably in methanol. Alternatively, the process can be carried out in the presence of a trialkylaluminum catalyst, preferably trimethylaluminum, in an aprotic solvent, preferably in toluene. The ratio of the compound of the formula (II) to the compound of the formula (III) is 2:0.7–1.3, preferably 2:0.9–1.1, particularly preferably 2:1. The reaction under acidic conditions in methanol/formic acid is generally preferred.

In general, the condensation is carried out at from 0 to 100° C., preferably from 15 to 80° C., particularly preferably from 20 to 40° C. The reaction time is generally from 20 minutes to 48 hours, preferably from 1 hour to 16 hours, particularly preferably from 2 hours to 14 hours. The precise reaction conditions are dependent on the compounds used in each case. In the case of compounds of the formulae (II) and (III) which condense only slowly to form the desired compounds of the formula (I), reaction in the presence of a trialkylaluminum catalyst in aprotic solvents may be preferred.

In a further preferred embodiment, the unsymmetrical 1,2-diimines of the formula (I) in which $R^1$≠$R^2$ are prepared in a two-stage process in which a) in a first step, compounds of the formula (II)

(II)

where $R^5$ and $R^6$ are as defined above are reacted with diketo compounds of the formula (III)

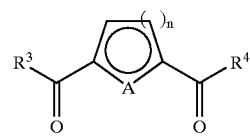

(III)

where $R^3$, $R^4$ are, independently of one another, H or alkyl, aryl or cycloalkyl radicals, and A is S, N, O or P, and n is 1 or 2, in a ratio of the compounds of the formula (II) to the compounds of the formula (III) of 1:0.8–1.2, preferably 1:0.9–1.1, particularly preferably 1:1, under acidic conditions, preferably with addition of mineral acids or organic acids, particularly preferably formic acid, in alcoholic solution, preferably methanol, to form the corresponding monoimine and the solvent is subsequently removed under reduced pressure, and b) the monoimine is, in a second step, reacted with compounds of the formula (II) which differ from the compounds of the formula (II) used in step a) or with compounds of the formula (IV)

$$H_2N\text{—}RN^7R^8 \qquad (IV)$$

where $R^7$ and $R^8$ are, independently of one another, alkyl, aryl or cycloalkyl radicals, or with amines of the formula (V)

$$R^{13}\text{-NH}_2 \qquad (V)$$

where $R^{13}$ is an alkyl, aryl or cycloalkyl radical, as defined above, in aprotic solution, preferably in toluene, in the presence of a trialkylaluminum catalyst, preferably trimethylol aluminum, in a ratio of the monoimine to the compound of the formula (II), (IV) or (V) of 1:0.8–1.2, preferably 1:0.9–1.1, particularly preferably 1:1.

In general, the condensation in step a) is carried out at from 0 to 100° C., preferably from 15 to 80° C., particularly preferably from 20 to 40° C. The reaction time is generally from 20 minutes to 48 hours, preferably from 1 hour to 16 hours, particularly preferably from 2 hours to 14 hours. The precise reaction conditions are dependent on the compounds used in each case. Step b) is generally carried out at from 0 to 100° C., preferably from 20 to 80°, particularly preferably from 30 to 60° C. The reaction time is generally from 20 minutes to 48 hours, preferably from 1 hour to 8 hours, particularly preferably from 2 hours to 7 hours. The precise reaction conditions are once again dependent on the compounds used in each case.

As compounds of the formula (II)

$$H_2N\text{—}NR^5R^6 \qquad (II)$$

where $R^5$ and $R^6$ are as defined above, particular preference is given to using compounds in which the group $NR^5R^6$ is a pyrrole radical or a radical derived from pyrrole which is very particularly preferably substituted in the 2 and positions by $C_1$–$C_6$-alkyl groups which may be linear, branched and be heteroatom-substituted, and/or by aryl groups which may be unsubstituted or in turn substituted by $C_1$–$C_6$-alkyl groups which may be heteroatom-substituted. Preferred substituents in the 2 and 5 positions of the pyrrole ring are methyl, i-propyl, t-butyl, phenyl or substituted aryl radicals, as defined above.

Such N-amino pyrroles can be obtained, for example, by the following two-stage process:

i) reaction of a suitable 1,4-diketone with an equivalent amount of acetylhydrazine or benzoyloxycarbonylhydrazine in the presence of a catalytic amount of acid, preferably p-toluenesulfonic acid, in an inert organic solvent, preferably toluene, to form the corresponding acetyl- or benzoyloxycarbonyl-protected N-aminopyrrole;

ii) hydrolysis of the protected N-aminopyrrole by means of an excess of base, preferably potassium hydroxide, in a high-boiling inert organic solvent, preferably ethylene glycol, under reflux to give the corresponding free N-aminopyrrole.

The subsequent work-up is carried out in a customary fashion.

The diketo compounds used in the process of the present invention are compounds of the formula (III);

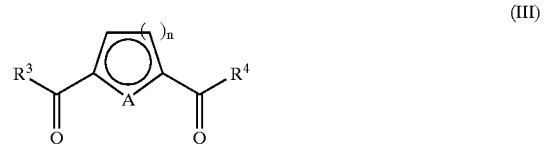

where $R^3$, $R^4$ are, independently of one another, H or alkyl, aryl or cycloalkyl radicals, with preferred radicals having been defined above; $R^3$ and $R^4$ are very particularly preferably H or $CH_3$; and A is S, N, O or P, preferably N or S, particularly preferably N, and n is 1 or 2, preferably 2.

The central heteroaromatic unit of the compounds of the formula (III) is thus preferably a pyridine ring which is substituted in the 2 and 6 positions.

The compounds of the present invention are suitable as ligands for catalysts which can be used for the polymerization of unsaturated compounds. The compounds of the present invention are particularly useful as ligands for catalysts containing a late transition metal, e.g. containing a metal of group 7, 8, 9 or 10 of the Periodic Table of the Elements. The present invention therefore also provides compounds of the formula (VI),

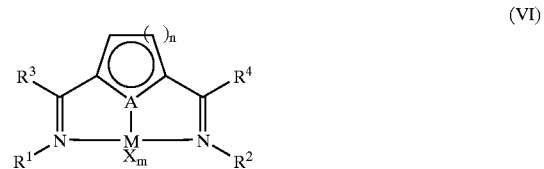

where the symbols have the following meanings:

A is a nonmetal selected from among N, S, O and P, $R^1$ is a radical of the formula $NR^5R^6$, $R^2$ is a radical of the formula $NR^5R^6$ or $NR^7R^8$, alkyl, aryl or cycloalkyl, $R^5$ and $R^6$ together with the N atom form a 5-, 6- or 7-membered ring in which one or more of the —CH— or —CH$_2$— groups may be replaced by suitable heteroatom groups and which may be saturated or unsaturated and unsubstituted or substituted or be fused with further carbacyclic or heterocarbacyclic 5- or 6-membered rings which may in turn be saturated or unsaturated and substituted or unsubstituted, and $R^7$ and $R^8$ are, independently of one another, alkyl, aryl or cycloalkyl radicals, and $R^3$, $R^4$ are, independently of one another, H or alkyl, aryl or cycloalkyl radicals, n is 1 or 2, M is a transition metal of groups 7, 8, 9 or 10 of the Periodic Table of the Elements, and X is a halide or a $C_1$–$C_6$-alkyl radical and m is the valence of the metal, preferably 2 or 3.

The transition metal M of group 7, 8, 9 or 10 of the Periodic Table of the Elements is preferably Ru, Mn, Co, Fe, Ni or Pd. These metals can be used in the following valences: Fe(II), Fe(III), Co(I), Co(II), Co(III), Ru(II), Ru(III), Ru(IV), Mn(I), Mn(II), Mn(III), Mn(IV), Ni(II), Pd(II). Particular preference is given to Fe and Co and m=2. The ligands X can be, independently of one another, halides or alkyl radicals. They are preferably chloride, bromide or methyl radicals. Particularly preferred moieties $MX_m$ are $MnCl_2$, $FeCl_3$, $CoCl_3$, $PdCl_2$, $NiCl_2$, $CoCl_2$, $FeCl_2$.

Preferred radicals $R^1$, $R^2$, $R^3$ and $R^4$ are as defined above.

Very particular preference is given to compounds of the formulae (VIa) to (VId):

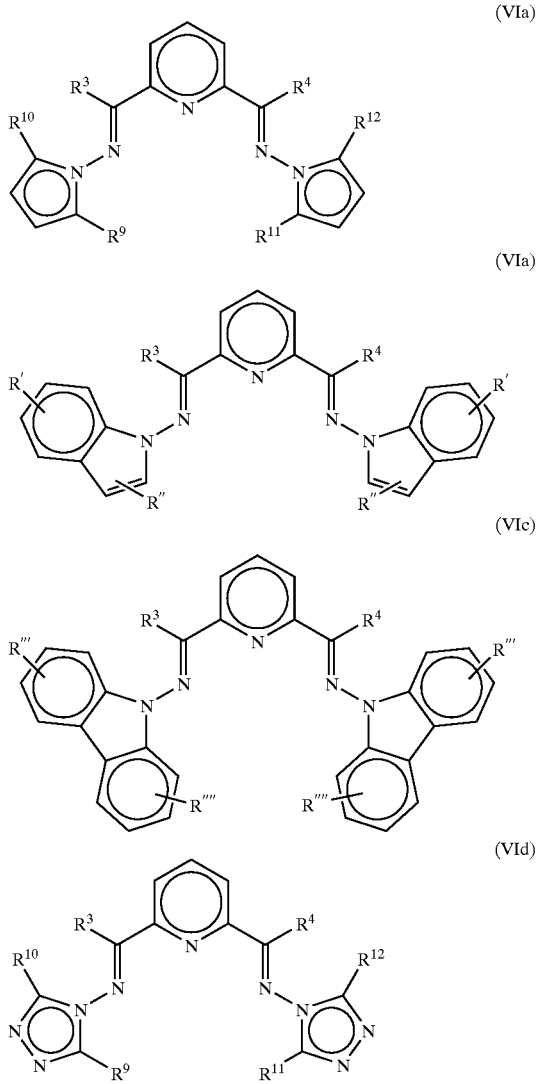

(VIa)

(VIc)

(VId)

where

R³, R⁴ are, independently of one another, H or alkyl or aryl radicals, with preferred radicals having been defined above, and $R^9$, $R^{10}$, $R^{11}$ and $R^{12}$ are, independently of one another, $C_1$–$C_6$-alkyl radicals, with preferred radicals having been defined above, and R', R", R''', R'''' are H or alkyl, aryl or cycloalkyl radicals, with preferred radicals having been defined above, and $MX^2$ is $MnCl_2$, $CoCl_2$ or $FeCl_2$, particularly preferably $FeCl_2$ and $CoCl_2$.

After activation with an activator (cocatalyst), these complexes are highly active in the polymerization of unsaturated compounds. The polymers obtained display a strong dependence on the structure of the ligand. Thus, small variations in the ligand make it possible to obtain a large number of catalytically active compounds which allow the preparation of polymers and oligomers having a wide spectrum of different properties.

The novel compounds of the formula (VI) are usually prepared by reacting the corresponding compounds of the formula (I) with salts of transition metals of groups 7, 8, 9 and 10 of the Periodic Table of the Elements.

In a preferred embodiment, a compound of the formula (I) which is suitable as ligand is combined in an organic solvent, e.g. tetrahydrofuran (THF) or methylene chloride, with an appropriate metal salt, e.g. $MnCl_2$, $FeCl_3$, $CoCl_3$, $CoCl_2$, $NiCl_2$, $PdCl_2$, $FeCl_2$, $FeCl_2$-THF complex. The molar ratio of ligand to metal salt is generally from 1.5:1 to 1:1.5, preferably from 1.2:1 to 1:1.2, particularly preferably about 1:1. The reaction mixture is generally stirred at temperatures from room temperature to 50° C., preferably from room temperature to 40° C., particularly preferably at room temperature, for generally from 0.5 hour to 16 hours, preferably from 1 to 6 hours, particularly preferably from 1 to 3 hours. The work-up is carried out in a customary manner, e.g. by removing the solvent under reduced pressure, washing of the residue with an inert solvent in which the residue (product) is largely insoluble, e.g. with diethyl ether, if desired digestion in a nonpolar solvent, e.g. hexane, filtration, washing and drying.

The novel metal complexes of the formula (VI) can be obtained easily and are suitable as catalysts for the polymerization of unsaturated compounds. They display a surprisingly high productivity in the polymerization or copolymerization of unsaturated compounds. Furthermore, in copolymerization, a number of the novel complexes enable a high incorporation of comonomer to be achieved. Even slight variations in the ligand skeleton of the metal complex enable the preparation of a wide range of polymers having different properties, so that it is possible to "tailor" a catalyst for a polymer having the desired properties.

For example, if iron complexes with 2,5-diisopropylpyrrole ligands are chosen, the polymerization of ethylene gives polymers having a relatively high molar mass in the region of $M_w$=about $10^5$.

Use of 2,5-dimethylpyrrole complexes of iron in the polymerization of ethylene at room temperature and atmospheric pressure gives oligomers having an $M_r$ of from 3000 to 3500 g/mol (determined by gel permeation chromatography (GPC)) and a molar mass distribution of Q=2–5, preferably Q=2–3, which is narrow for single-site catalysts. A particular feature of these oligomers is their unusual structure. They display a particularly high degree of branching, which can also be observed in the homopolymerization of ethylene. The very high proportion of branches longer than 6 carbon atoms is particularly conspicuous. In the case of other catalyst systems (i.e. other than the catalyst systems of the present invention) which give polyolefins having a high degree of branching (e.g. Ni- and Pd-diimine systems), methyl branches are by far the most abundant and only a small number of longer branches is present. Furthermore, the oligomers prepared according to the present invention also have a large number of unsaturated end groups which make it possible for them to be used as monomers in polymerizations or to be functionalized chemically.

Variation of the ligand, e.g. iron complex having a carbazole substituent, enables relatively short-chain oligomers (liquids) to be obtained.

Other catalyst systems, e.g. Co complexes containing carbazole groups, give only very short-chain oligomers which generally have from 6 to 18 carbon atoms, preferably a maximum of 8 carbon atoms.

In the copolymerization of a-olefins, the use of, for example, an iron-isopropylmethylpyrrole system gives excellent incorporation of, for example, hexene.

A simple variation of the ligand framework thus provides catalysts for preparing a wide variety of polymers. In addition, these catalysts display a very high activity which in many cases exceeds that of comparable systems. Furthermore, cobalt complexes having an extremely high activity have been found. The activity of Co complexes known from the literature is usually at least a factor of ten less than that of analogous Fe complexes (V. C. Gibson et al., Chem. Commun. 1998, 849–850 and M. Brookhart et al., J. Am. Chem. Soc. 1998, 120, 4049–4050).

Accordingly, the present invention further provides for the use of compounds of the formula (VI) as catalysts in a process for the polymerization of unsaturated compounds and provides a process for preparing polyolefins by polymerization of unsaturated compounds in the presence of a catalyst according to the present invention and an activator.

Particularly useful activators (cocatalysts) are strong, uncharged Lewis acids, ionic compounds having Lewis acid cations and ionic compounds having Bronsted acids as cations.

As strong, uncharged Lewis acids, preference is given to compounds of the formula (VII), $$M'X^1X^2X^3 \quad (VII)$$

where the symbols have the following meanings:

M' is an element of main group III of the Periodic Table of the Elements, preferably B, Al or Ga, particularly preferably B, $X^1$, $X^2$, $X^3$ are each, independently of one another, hydrogen, $C_1$–$C_{10}$-alkyl, $C_6$–$C_{15}$-aryl, alkylaryl, arylalkyl, haloalkyl or haloaryl each having from 1 to 10 carbon atoms in the alkyl radical and from 6 to 20 carbon atoms in the aryl radical, or fluoride, chloride, bromide or iodide; preference is given to haloaryls, particularly preferably pentafluorophenyl.

Very particular preference is given to compounds of the formula (VII) in which $X^1$, $X^2$, $X^3$ are identical, preferably tris(pentafluorophenyl)borane.

A further preferred uncharged Lewis acid for use as activator (cocatalyst)) is "$R^{14}$AlO" (alkylaluminoxane), where $R^{14}$ is a $C_1$–$C_{25}$-alkyl radical, preferably a $C_1$–$C_4$-alkyl radical, particularly preferably a methyl radical (methylaluminoxane).

Suitable ionic compounds having Lewis acid cations are compounds of the formula (VIII),

where the symbols have the following meanings

Y is an element of main groups I to VI or transition groups I to VIII of the Periodic Table of the Elements, $Q_1$, to $Q_z$ are singly negatively charged groups such as $C_1$–$C_{28}$-alkyl, $C_6$–$C_{15}$-aryl, alkylaryl, arylalkyl, haloalkyl, haloaryl each having from 6 to 20 carbon atoms in the aryl radical and from 1 to 28 carbon atoms in the alkyl radical, $C_1$–$C_{10}$-cycloalkyl which may be unsubstituted or bear $C_1$–$C_{10}$-alkyl groups as substituents, halide, $C_1$–$C_{28}$-alkoxy, $C_6$–$C_{15}$-aryloxy, silyl or mercaptyl groups, a is an integer from 1 to 6, z is an integer from 0 to 5, d is the difference a–z, but d is greater than or equal to 1.

Particular preference is given to carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis (pentafluorophenyl)borate.

Ionic compounds having Bronsted acids as cation and preferably likewise noncoordinating counterions are likewise mentioned in WO 91/09882; a preferred cation is N,N-dimethylanilinium.

The amount of activator is preferably from 0.1 to 10 equivalents, particularly preferably from 1 to 2 equivalents, for borates, based on the catalyst (VI). For alkylaluminoxanes, in particular methylaluminoxane, the amount of activator is generally from 50 to 1000 equivalents, preferably from 100 to 500 equivalents, particularly preferably from 100 to 300 equivalents, based on the catalyst (VI).

The polymerization process of the present invention is suitable for preparing homopolymers or copolymers. As unsaturated compounds or combinations of unsaturated compounds, preference is given to using unsaturated compounds selected from among ethylene, $C_3$–$C_{20}$-monoolefins, ethylene and $C_3$–$C_{20}$-monoolefins, cycloolefins, cycloolefins and ethylene and cycloolefins and propylene. Preferred $C_3$–$C_{20}$-monoolefins are propylene, butene, hexene and octene and preferred cycloolefins are norbornene, norbornadiene and cyclopentene.

The abovementioned monomers can be copolymerized with monomers containing a carbonyl group, e.g. esters, carboxylic acids, carbon monoxide and vinyl ketones. The following combinations of unsaturated compounds are preferred: ethylene and an alkyl acrylate, in particular methyl acrylate, ethylene and an acrylic acid, ethylene and carbon monoxide, ethylene, carbon monoxide and an acrylate ester or an acrylic acid, in particular methyl acrylate, and also propylene and alkyl acrylate, in particular methyl acrylate. Further suitable comonomers are acrylonitrile and styrene.

Depending on the reaction conditions and the monomers used, it is possible to obtain homopolymers, random copolymers or block copolymers by means of the process of the present invention.

The polymerization is carried out under generally customary conditions in solution, e.g. as a high-pressure polymerization in a high-pressure reactor or high-pressure autoclave, in suspension or in the gas phase (e.g. GPWS polymerization process). The appropriate polymerization processes can be carried out as batch processes, semicontinuously or continuously, with the procedures being known from the prior art.

The catalyst systems used according to the present invention can be employed in the form of all-active catalysts or supported catalysts, depending on the polymerization conditions.

As support materials, preference is given to using finely divided solids whose particle diameter is in the range of generally from 1 to 200 mm, preferably from 30 to 70 mm.

Suitable support materials are, for example, silica gels, preferably those of the formula $SiO_2.aAl_2O_3$, where a is in the range from 0 to 2, preferably from 0 to 0.5; these are thus aluminosilicates or silicon dioxide. Such products are commercially available for example silica gel 332 from Grace or ES 70x from Crosfield.

To remove adsorbed water, these support materials can be subjected to a thermal or chemical treatment or be calcined; preference is given to carrying out a thermal treatment at from 80 to 200° C., particularly preferably from 100 to 150° C.

Other inorganic compounds such as $Al_2O_3$ or $MgCl_2$ or mixtures comprising these compounds can likewise be used as support materials.

The catalysts of the formula (VI) can be prepared in situ and used directly, without prior isolation, in the polymerization. The catalysts can also be prepared in situ in the presence of the support material.

Suitable solvents are, in particular, aprotic organic solvents. For the catalyst system, the monomer or monomers and the polymer can be soluble or insoluble in these solvents, but the solvents should not participate in the polymerization. Examples of suitable solvents are alkanes, cycloalkanes, selected halogenated hydrocarbons and aromatic hydrocarbons. Preferred solvents are hexane, toluene and benzene; particular preference is given to toluene.

The polymerization temperatures in the solution polymerization are generally in a range from −20 to 350° C., preferably from 0 to 350° C., particularly preferably from +20 to 180° C, very particularly preferably from room temperature to 80° C. The reaction pressure is generally from 0.1 to 5000 bar, preferably from 0.1 to 3000 bar, particularly preferably from 1 to 200 bar, very particularly preferably from 5 to 40 bar. The polymerization can be carried out in any apparatus suitable for the polymerization of unsaturated compounds.

To control the molecular weight of the polymers, the polymerization can be carried out in the presence of hydrogen gas which acts as chain transfer reagent. The mean molecular weight usually decreases with increasing hydrogen concentration.

In addition, further auxiliaries customary in the respective polymerization process can be used.

The polymerization process of the present invention opens up a route to polyolefins having novel structures and properties. The present invention therefore further provides polymers which can be prepared by the process of the present invention.

The following examples illustrate the invention.

EXAMPLES

The Numbering of the Compounds in the Examples is Independent of the Numbering of the Compounds in the Description Above a) Synthesis of 1,4-diketones (FIG. 1)

Acetonylacetone (1) is commercially available (Aldrich); the ketones 2–7 were synthesized by literature methods (T. Saegusa, Y. Ito, T.Konsoke, J. Am. Chem. Soc., 97 (1975) 2912; H. Stetter, M. Schreckenberger, Chem. Ber., 107 (1974) 2453; H. Stetter, H. Kuhlmann, Chem. Ber., 109 (1976) 3426; H. Stetter, Angew. Chem., 21 (1976) 695; H. Stetter, F. Jonas, Chem. Ber., 114 (1981) 564).

1-(2-Methylphenyl)pentane-1,4-dione (5):

25 g (208 mmol) of o-tolualdehyde, 14.58 g (208 mmol) of methyl vinyl ketone, 21.05 g (208 mmol) of triethylamine, 5.4 g (21.4 mmol) of 3-ethyl-5-(2-hydroxyethyl)-4-methylthiazolium bromide were dissolved in this order in 100 ml of DMF and stirred at 80° C. for 12 hours. The reaction mixture was subsequently admixed with 400 ml of water and extracted twice with methylene chloride. The combined methylene chloride phases were washed with 10% strength sulfuric acid and saturated sodium hydrogencarbonate solution and dried over sodium sulfate. After taking off the solvent on a rotary evaporator, the product was purified by fractional distillation.

Yield: 20.52 g (107 mmol), 52%, $C_{12}H_{14}O_2$, boiling point: 93–96° C. (high vacuum), $^1$H NMR ($CDCl_3$): δ 2.07 (m 3H $CH_3$), 2.34 (s 3H $CH_3$), 2.68 (m 2H $CH_2$), 2.98 (m 2H $CH_2$), 7.09–7.58 (m 4H phenyl); M+=190 m/e.

b) General Method for the Synthesis of Protected Pyrroles (FIG. 1) (8–11)

5–15 g of a 1,4-diketone (3–7), 10 mg of p-toluenesulfonic acid and 1.5 equivalents of acetylhydrazide were refluxed in 100 ml of toluene for 48 hours using a water separator. After cooling, the precipitate formed was either filtered off from the reaction mixture or extracted by means of methylene chloride.

1-Acetamido-2-methyl-5-phenylpyrrole (8):

Reaction conditions: 48 hours reflux, extraction with methylene chloride.

Yield: 4.3 g (25 mmol), 51%, $C_{13}H_{14}N_2O$, melting point: 159° C., $^1$H NMR (DMSO-$d_6$): δ 1.27 (s 3H methyl), 1.37 (s 3H methyl), 5.19 (d $^1$H pyrrole), 5.47 (d 1H pyrrole), 6.53–6.80 (m, 5H phenyl), 10.16 (s 1H N—H); MS: $M^+$=214 m/e.

1-Acetamido-2-methyl-5-isopropylpyrrole (9):

Reaction conditions: 48 hours reflux, extraction with methylene chloride. Yield: 8.11 g (45 mmol), 53%; $C_{10}H_{16}N_2O$, melting point: 81° C., $^1$H NMR (DMSO-$d_6$): δ 1.06 (d 3H $CH(CH_3)_2$) (J=7 Hz), 1.11 (d 3H $CH(CH_3)_2$) (J=7 Hz), 1.95 (s 3H $CH_3$), 2.00 (s 3H $CH_3$), 2.63 (m 1H $CH(CH_3)_2$), 5.60 (d 1H pyrrole), 5.63 (d 1H pyrrole), 10.13 (s broad 1H N—H); MS: $M^+$=180 m/e.

1-Acetamido-2-methyl-5-(2-methylphenyl)pyrrole (10):

Reaction conditions: 37 hours reflux, extraction with methylene chloride.

Yield: 10.3 g (45 mmol), 37%, $C_4H16N_2O$, melting point: 146° C., $^1$H NMR ($CDCl_3$), δ 1.52, 1.88; 2.15; 2.20; 2.25, 2.26 (s, 9H, $CH_3$); 5.97, 6.04 (m, 2H, pyrrole-H); 7.14–7.23 (m, 4H, phenyl-H); 7.65–7.82 (br. s, 1H, N—H). According to the NMR spectrum, a mixture of two isomers in a ratio of 0.8:1 is present. MS: M+=228 m/e.

1-Acetamido-2,3,5-triphenylpyrrole (11):

Reaction conditions: 48 hours reflux, precipitate formed after cooling filtered off. Yield: 38%, $C_{24}H_{20}N_2O$, melting point: 255° C., $^1$H NMR ($CDCl_3$): δ 1.25 (s 3H methyl), 6.01 (8 1H pyrrole), 6.58–6.95 (m 15H phenyl), 8.08 (s 1H N—H); MS: $M^+$=352 m/e.

c) General Method for the Synthesis of Amino Pyrroles (FIG. 1) (12–18)

5–15 g of amide (8–11) were refluxed with 10 equivalents of potassium hydroxide in glycol until reaction was complete (monitoring by TLC). Addition of 200 ml of water and subsequent repeated extraction with methylene chloride gives the product an analytically pure form.

1-Amino-2-methyl-5-phenylpyrrole (14):

Reaction conditions: 36 hours reflux.

Yield: 2.82 g (16.3 mmol), 88%, $C_{11}H_{12}N_2$, melting point: 92° C., $^1$H NMR (DMSO-$d_6$): δ 2.23 (s 3H methyl), 5.48 (s 2H $NH_2$), 5.75 (d 1H pyrrole), 6.04 (d 1H pyrrole), 7.05–7.68 (m 5H phenyl); MS: $M^+$=172 m/e.

1-Amino-2-methyl-5-isopropylpyrrole (15):

Reaction conditions: 16 hours reflux.

Yield: 5.43 g (39.3 mmol), 88%, $C_9H_{14}N_2$, melting point: 21–24° C., $^1$H NMR ($CDCl_3$): δ 1.24 (d 6H $CH(CH_3)_2$ J=7 Hz), 2.23 (s 3H $CH_3$), 3.10 (septet 1H $CH(CH_3)_2$, 4.09 (9 broad 2H $NH_2$), 5.70 (d 1H pyrrole J=3 Hz), 5.74 (d 1H pyrrole J=3 Hz); MS: $M^+$=138 m/e.

1-Amino-2-methyl-5-(2-methylphenyl)pyrrole (16):

Reaction conditions: 12 hours reflux.

Yield: 7.54 g (33 mmol), 37%, $C_{14}H_{16}N_2O$, melting point: 146° C., $^1$H NMR (CDCl$_3$): (2 isomers in a ratio of 0.8:1) δ 1.52 (s 3H CH$_3$), 1.88 (s 3H CH$_3$), 2.15 (s 3H CH$_3$), 2.19 (s 3H CH$_3$), 2.24 (s 3H CH$_3$), 2.26 (s 3H CH$_3$), 5.95–6.06 (m 4H pyrrole), 7.13–7.23 (m 8H phenyl), 7.65 (s 1H broad N—H), 7.82 (s 1H broad N—H); MS: M$^+$=228 m/e.

1-Amino-2,3,5-triphenylpyrrole (18):

Reaction conditions: 36 hours reflux.

Yield: 2.62 g (8.4 mmol), 85%, $C_{22}H_{18}N_2$, melting point: 179° C., $^1$H NMR (CDCl$_3$): δ 5.53 (s 2H NH$_2$), 6.46 (s 1H pyrrole), 7.05–7.79 (m 15H phenyl); MS: M$^+$=310 m/e.

d) General method for the synthesis of 2,6-diacetylpyridinebis(2,5-R-azol-1-ylimines) (FIG. 2) (22–31)

2–3 g of an N-aminoazole (12–21) (2.2 meq) and one molar equivalent of diacetylpyridine were firstly dissolved in very little methanol (4–8) ml and stirred with a few drops of formic acid for at least 12 hours. Depending on the substitution on the pyrrole, it may also be necessary to reflux the reaction solution. The diimine could in most cases be filtered off at the end of the reaction and dried in a high vacuum. In some cases, N-aminopyrrole was added to complete the reaction, or the diimine was recrystallized from a suitable solvent to separate off the monoimine. Diphenylaminopyrrole and triphenylaminopyrrole were refluxed in propionic acid for up to 48 hours. Reaction conditions, yield and spectroscopic data are shown for the individual compounds.

2,6-Diacetylpyridinebis(2,5-dimethylpyrrol-1-ylimine) (22):

Procedure as described above:

Reaction conditions: room temperature: 16 hours; the diimine was filtered off, washed with cold methanol and dried in a high vacuum; yield 77.1%, melting point: 174–178° C.; $C_{21}H_{25}N_5$; $^1$H NMR (CDCl$_3$): δ 2.1 (s 12H methyl), 2.45 (s 6H CH$_3$C=N), 5.95 (s 4H pyrrole), 7.95 (t 1H p pyridine), 8.51 (d 2H m pyridine); MS: M$^+$=347 m/e.

2,6-Diacetylpyridinebis-(2,5-diisopropylpyrrol-1-ylimine) (23):

Procedure as described above:

Reaction conditions: room temperature 12 hours, reflux 2 hours; the diimine was filtered off at room temperature, washed with methanol and dried in a high vacuum; yield 72.5%, melting point: 198–203° C.; $C_{29}H_{41}N_5$; $^1$H NMR (CDCl$_3$): δ 1.20 (d 24H CH(CH$_3$), 2.32 (s 6H CH$_3$C=N), 2.64 (m 4H CH(CH$_3$)), 5.94 (s 4H pyrrole), 7.95 (t 1H p pyridine), 8.51 (d 2H m pyridine); MS: M$^+$=460 m/e.

2,6-Diacetylpyridinebis-(2-methyl-5-phenylpyrrol-1-ylimine) (24):

0.71 g (4.4 mmol) of diacetylpyridine and 3 drops of formic acid were added to a solution of 1.5 g (8.7 mmol) of 1-amino-2-methyl-5-phenylpyrrole (14) in 30 ml of methanol. After refluxing for four days, the reaction mixture was cooled to −18° C. and the resulting precipitate was filtered off. After concentration by evaporation and cooling again, all of the product could be separated off.

Yield: 0.83 g (1.8 mmol), 40%, $C_{31}H_{29}N_5$, melting point: 115° C.; $^1$H NMR (DMSO-d$_6$): δ 1.99 (s 6H methyl), 2.06 (s 6H methyl), 6.00 (d 2H pyrrole), 6.31 (d 2H pyrrole), 7.04–7.38 (m 10H phenyl) 8.16 (m 2H pyridine), 8.47 (m 2H pyridine); MS: M$^+$=471 m/e.

2,6-Diacetylpyridinebis-(2-methyl-5-isopropylpyrrol-1-ylimine) (25):

1.59 g (9.7 mmol) of diacetylpyridine and 5 drops of formic acid were added to a solution of 2.71 g (19.5 mmol) of 1-amino-2-methyl-5-isopropylpyrrole (15) in 50 ml of methanol. After refluxing for four days, the reaction mixture was cooled to −18° C. and the resultant precipitate was filtered off. After concentration by evaporation and cooling again, all of the product could be separated off.

Yield: 1.94 g (4.8 mmol), 49%, $C_{25}H_{33}N_5$, melting point: 54° C.; $^1$H NMR (CDCl$_3$): δ 1.19 (d 12H CH(CH$_3$)$_2$ J=7 Hz), 2.05 (s 6H CH$_3$), 2.35 (s 3H CH$_3$), 2.73 (m 1H CH(CH$_3$)$_2$), 5.89–5.92 (m 4H pyrrole), 7.93 (t 1H pyridine), 8.47 (d 2H pyridine) MS: M$^+$=403 m/e.

2,6-Diacetylpyridine-bis-(2-methyl-5-(2-methylphenyl)pyrrol-1-ylimine) (26):

2 g (11 mmol) of 1-amino-2-methyl-5-(2-methylphenyl)pyrrole (16), 876 mg (5.4 mmol) of diacetylpyridine and three drops of formic acid were refluxed in 30 ml of methanol for 48 hours. The reaction mixture was subsequently cooled to 0° C., the resulting precipitate was filtered off and was washed a number of times with cold methanol.

Yield: 2.44 g (4.9 mmol), 91%, $C_{33}H_{33}N_5$, melting point: 58° C.; $^1$H NMR (CDCl$_3$): δ 2.13 (s 3H CH$_3$), 2.38 (s 3H CH$_3$), 2.56 (s 3H CH$_3$), 6.27 (m 2H pyrrole), 6.35 (m 2H pyrrole), 7.23–7.46 (m 8H phenyl), 8.00 (t 1H pyridine), 8.44 (d 2H pyridine) MS: M$^+$=499 m/e.

2,6-Diacetylpyridinebis-(2,5-diphenylpyrrol-1-ylimine) (27):

3 g (12.8 mmol) of 1-amino-2,5-diphenylpyrrole (17) and 1.04 g (6.4 mmol) of diacetylpyridine were refluxed in propionic acid for 12 hours. After the reaction mixture had cooled, it was evaporated to half its volume, the resulting precipitate was filtered off and was washed a number of times with methanol.

Yield: 0.75 g (1.3 mmol), 10.2%, $C_{41}H_{33}N_5$, melting point: 228–231° C.; $^1$H NMR (CDCl$_3$): δ 1.70 (s 6H methyl), 6.44 (s 4H pyrrole), 7.07–7.50 (m 20H phenyl), 7.88 (m 1H pyridine), 8.38 (m 2H pyridine); MS: M$^+$=595 m/e.

2,6-Diacetylpyridinebis(2,3,5-triphenylpyrrol-1-ylimine) (28):

1.5 g (4.8 mmol) of 1-amino-2,3,5-triphenylpyrrole (18) and 0.39 g (2.4 mmol) of diacetylpyridine were refluxed in 20 ml of propionic acid for 2 days. After cooling and taking off the solvent on a rotary evaporator, the residue was dissolved in ethanol and crystallized at −18° C. After concentration by evaporation and renewed crystallization, all of the product could be isolated.

Yield: 0.83 g (1.1 mmol), 47%, $C_{53}H_{41}N_5$, melting point: 132° C; $^1$H NMR (DMSO-d6): δ 1.68 (s 6H methyl), 6.75 (s 2H pyrrole), 7.00–7.51 (m 30H phenyl), 8.04 (m 1H pyridine), 8.24 (m 2H pyridine); MS: M$^+$=747 m/e.

2,6-diacetylpyridinebis(2-methylindol-1-ylimine) (29):

0.71 g (4.9 mmol) of 1-amino-2-methylindole (19) (M. Somei, M. Natsume, Tetrahedron Lett., 5 (1974) 461) dissolved in 10 ml of methanol were admixed with 0.4 g 2.4 mmol) of diacetylpyridine and subsequently refluxed for 12 hours. The resulting precipitate was filtered off and washed a number of times with cold methanol.

Yield: 0.75 g (1.8 mmol), 73%, $C_{27}H_{25}N_5$, melting point: 65° C., $^1$H NMR (CDCl$_3$): δ 2.43 (s 6H methyl), 2.53 (s 6H methyl), 6.43 (d 2H pyrrole), 6.96–8.55 (m 11H phenyl, pyridyl); MS: M$^+$=420 m/e.

2,6-Diacetylpyridinedicarbazol-N-ylimine (30):

2–3 g of N-aminocarbazole (20) (J. Klein, L. Davis, G. Olsen, G. Wong, F. Huger, J. Med. Chem., 39 (1996) 570) (2.2 equivalents) and one equivalent of diacetylpyridine were dissolved in a little methanol (5 ml) and refluxed for 8 hours (1 ml of formic acid were added beforehand). The solution was allowed to cool and the diimine was filtered off. Drying in a high vacuum gave the product in a yield of 75.1%.

Melting point: 184–188° C.; $C_{33}H_{25}N_5$; $^1$H NMR (CDCl$_3$): δ 2.61 (s 6H CH$_3$C=N), 7.95 (t 1H p pyridine), 8.51 (d 2H m pyridine), 7.2 (m 8H) 7.4 (m 4H) 8.1 (m 4H) carbazole; MS: M$^+$=491 m/e.

2,6-Diacetylpyridinebis(3,5-dimethyl-1,2,4-triazol-4-ylimine) (31):

960 mg of 4-amino-3,5-dimethyl-1,2,4-triazole (21) (R. Herbst, J. Garrison, J. Org. Chem., 18, (1953), 872–876) and 698 mg of 2,6-diacetylpyridine and 30 mg of p-toluenesulfonic acid were refluxed in 30 ml of o-dichlorobenzene for 8 hours. After cooling, a 1:1 mixture of hexane/ether was slowly added while stirring well to precipitate the diimine. The supernatant solution was decanted off, the brownish powder was digested once more, the supernatant solution was decanted off again and the product was then dried in a high vacuum. Yield: 1.41 g (94.0%), melting point: 252° C. with decomposition; $C_{17}H_{21}N_9$; $^1$H NMR (CD$_3$CN): δ 2.25 (s 12H methyl), 2.58 (s 6H CH$_3$C=N), 8.11 (t 1H p pyridine), 8.45 (d 2H m pyridine); MS: M$^+$=351 m/e.

2,5-Diformylthiophenebis(2,5-diisopropylpyrrol-1-ylimine): (FIG. 2) (32)

474 mg of N-amino-2,5-diisopropylpyrrole (13) and 200 mg of 2,5-diformylthiophene were dissolved in 10 ml of methanol and refluxed for 2 hours (0.5 ml of formic acid were added beforehand). The solution was allowed to cool and the diimine was filtered off. Drying in a high vacuum gave 510 mg (81.8%) of product.

Melting point: 134–137° C.; $C_{26}H_{36}N_4S$; $^1$H NMR (CDCl$_3$): δ 1.00 (s 24H CH(CH$_3$), 2.81 (m 4H CH(CH$_3$)), 5.68 (s 4H pyrrole), 7.12 (s 2H thiophene), 8.24 (s 2H formyl); MS: M$^+$=437 m/e.

e) Metal Complexes (FIG. 3) (34–52)

[2,6-Diacetylpyridinebis-(2,5-dimethylpyrrol-1-ylimine)]FeCl$_2$ (34):

20 ml of 2-butanol were placed in a dry Schlenk tube and argon was introduced via a glass frit for 5 minutes until the solvent had been completely saturated with argon. 200 mg of 2,6-diacetylpyridinebis(2,5-methylpyrrol-1-ylimine) (22) and 73 mg of iron(II) chloride were then added and the mixture was heated at 80° C. for 1 hour. The solution immediately became dark green and a precipitate of the same color was formed. After cooling, the precipitate was allowed to settle and the supernatant solution was decanted off. The remainder of the 2-butanol was taken off under a high vacuum, the residue was pulverized and extracted a number of times with absolute methylene chloride. The green methylene chloride phase was taken off, residue 195 mg (72%); $C_{21}H_{25}N_5FeCl_2$; Mr: 474.2 g/mol; NMR: paramagnetic; MS: M$^+$=474 m/e.

[2,6-Diacetylpyridinebis(2,5-dimethylpyrrol-1-ylimine)]FeCl$_3$ (35):

20 ml of absolute methylene chloride, 367 mg of 2,6-diacetylpyridinebis(2,5-methylpyrrol-1-ylimine) (22) and 175 mg of iron(III) chloride were placed in a dry Schlenk tube; the solution immediately became dark brown and a precipitate of the same color was formed. After stirring at room temperature for 15 hours, the methylene chloride was taken off in a high vacuum and the brown residue was digested twice with absolute hexane (10 ml) and the hexane was in each case decanted off. The product obtained this way was dried in a high vacuum. Yield: 420 mg (78.0%), $C_{21}H_{25}N_5FeCl_3$; Mr: 509.6 g/mol; NMR: paramagnetic.

[2,6-Diacetylpyridinebis(2,5-dimethylpyrrol-1-ylimine)]CoCl$_2$ (36):

10 ml of 2-butanol were placed in a dry Schlenk tube and argon was introduced via a porcelain frit for 5 minutes until the solvent was completely saturated with argon. 150 mg of 2,6-diacetylpyridinebis(2,5-methylpyrrol-1-ylimine) (22) and 56 mg of cobalt(II) chloride were then added and the mixture was heated at 80° C. for 1 hour. The solution immediately became dark brown and a precipitate of the same color was formed. After cooling, the precipitate was allowed to settle and the supernatant solution was decanted off. The remainder of the 2-butanol was taken off in a high vacuum and the residue was pulverized. Yield: 155 mg (75.2%); $C_{21}H_{25}N_5CoCl_2$; Mr: 477.3 g/mol; NMR: paramagnetic.

[2,6-Diacetylpyridinebis-(2,5-diisopropylpyrrol-1-ylimine)]FeCl$_2$ (37):

30 ml of 2-butanol were placed in a dry Schlenk tube and flushed with argon for 5 minutes. After addition of 1.0 g of 2,6-diacetylpyridinebis(2,5-diisopropylpyrrol-1-ylimine) (23) and 274 mg of iron(II) chloride, the dark green solution was stirred at 80° C. for 2 hours. The solvent was then taken off in a high vacuum, the residue was pulverized and extracted a number of times with 100 ml of absolute methylene chloride. After taking off the methylene chloride, 1.04 g (81.5%) of green powder remained. $C_{29}H_{41}N_5FeCl_2$; Mr: 586.4 g/mol; NMR: paramagnetic.

[2,6-Diacetylpyridinebis(2,5-diisopropylpyrrol-1-ylimine)]FeCl$_3$ (38):

20 ml of absolute methylene chloride, 400 mg of 2,6-diacetylpyridinebis(2,5-diisopropylpyrrol-1-ylimine) (23) and 141 mg of iron(III) chloride were placed in a dry Schlenk tube; the solution immediately became dark brown. After stirring at room temperature for 15 hours, the methylene chloride was taken off in a high vacuum and the brown residue was digested twice with absolute hexane (10 ml) and the hexane was decanted off in each case. The product obtained in this way was dried in a high vacuum. Yield: 461 mg (85.2%), $C_{29}H_{41}N_5FeCl_3$, Mr: 621.9 g/mol, NMR: paramagnetic.

[2,6-Diacetylpyridinebis(2,5-diisopropylpyrrol-1-ylimine)]CoCl$_2$ (39):

50 ml of absolute tetrahydrofuran, 500 mg of 2,6-diacetylpyridinebis(2,5-diisopropylpyrrol-1-ylimine) (23) and 141 mg of cobalt(II) chloride were placed in a dry Schlenk tube. The solution immediately became dark brown and a precipitate of the same color was formed. After stirring for 12 hours, the solvent was taken off in a high vacuum, the brown residue was digested twice with absolute hexane and the supernatant solution was decanted off each time, and the residue was dried. Yield: 450 mg (70.2%); $C_{29}H_{41}N_5CoCl_2$; Mr: 589.5 g/mol.

[2,6-Diacetylpyridinebis-(2-methyl-5-phenylpyrrol-1-ylimine)]FeCl$_2$ (40):

A solution of 0.14 g (1.1 mmol) of iron(II) chloride and 0.48 g (1.0 mmol) of 2,6-diacetylpyridinebis(2-methyl-5-phenylpyrrol-1-ylimine) (24) in 30 ml of 2-butanol was stirred overnight at 40° C. The resulting precipitate was filtered off under argon and washed a number of times with absolute ether.

Yield: 0.23 g (0.4 mmol), 37%, $C_{31}H_{29}FeCl_2N_5$, melting point: >350° C. (decomp.); IR: KBr (cm$^{-1}$) 3071(w), 2919 (w), 1640(s), 1605(s), 1514(m), 1445(m), 1373(s), 1298(w), 1273(w), 1204(w), 1074(w), 1026(w), 810(w), 756(s), 698 (m), 605(w), 565(w), 497(w).

[2,6-Diacetylpyridinebis(2-methyl-5-phenylpyrrol-1-ylimine)]CoCl$_2$ (41):

0.41 g (0.9 mmol) of diacetylpyridinebis(2-methyl-5-phenylpyrrol-1-ylimine) (24) and 0.12 g (0.9 mmol) of cobalt(II) chloride were dissolved in 30 ml of THF and subsequently stirred at room temperature for twelve hours.

After complete precipitation by means of ether and washing the filtered product a number of times with ether, the compound can be obtained in analytically pure form.

Yield: 0.29 g (0.5 mmol), 54%, $C_{31}H_{29}Cl_2CoN_5$, melting point: >350° C. (decomp.); IR: KBr ($cm^{-1}$) 3071(w), 3031 (w), 2917(w), 1601(m), 1576(m), 1514(s), 1474(w), 1445 (m), 1375(s), 1331(s), 1300(w), 1271(m), 1205(w), 1180 (w), 1026(m), 810(w), 752(s), 729(m), 698(s); MS: M+−Cl= 566 m/e.

[2,6-Diacetylpyridinebis-(2-methyl-5-isopropylpyrrol-1-ylimine)]$FeCl_2$ (42):

A solution of 0.27 g (2.1 mmol) of iron(II) chloride and 0.86 g (2.1 mmol) of 2,6-diacetylpyridinebis(2-methyl-5-isopropylpyrrol-1-ylimine) (25) in 150 ml of 2-butanol was stirred overnight at 40° C. The resulting precipitate was filtered off under argon and washed a number of times with absolute ether.

Yield: 0.82 g (1.5 mmol), 72%, $C_{25}H_{33}FeCl_2N_5$, melting point: >350° C. (decomp.); IR: KBr ($cm^{-1}$) 2963(s), 2925(s), 2871(m), 1615(w), 1578(s), 1449(w), 1402(s), 1373(s), 1362(m), 1267(s), 1223(w), 1202(m), 1105(w), 1026(m), 812(m), 748(s).

[2,6-diacetylpyridinebis-(2-methyl-5-isopropylpyrrol-1-ylimine)]$CoCl_2$ (43):

0.8 g (2.0 mmol) of diacetylpyridinebis-(2-methyl-5-isopropylpyrrol-1-ylimine) (25) and 0.26 g (2.0 mmol) of cobalt(II) chloride were suspended in 15 ml of THF and the mixture was subsequently stirred at room temperature for 12 hours. Complete precipitation by means of ether and washing the filtered product a number of times with ether gives the compound in analytically pure form.

Yield: 0.99 g (1.9 mmol), 94%, $C_{25}H_{33}Cl_2CoN_5$, melting point: >350° C. (decomp.); IR: KBr ($cm^{-1}$) 2963(s), 2925 (m), 2871(m), 1624(m), 1578(s), 1447(w), 1402(s), 1373(s), 1362(s), 1333(w), 1269(s), 1204(w), 1103(w), 1026(m), 812(m), 748(s); MS: M+−Cl=498 m/e.

[2,6-Diacetylpyridinebis(2-methyl-5-(2-methylphenyl) pyrrol-1-ylimine)]$FeCl_2$ (44):

0.98 g (2 mmol) of 2,6-diacetylpyridinebis(2-methyl-5-(2-methylphenyl)pyrrol-1-ylimine) (26) and 0.25 g (2 mmol) of iron(II) chloride were stirred in 40 ml of argon-saturated 2-butanol at 40° C. for 12 hours. The resulting precipitate was then filtered off and washed a number of times with ether.

Yield: 0.80 g (1.3 mmol), 65%, $C_{33}H_{33}FeCl_2N_5$, melting point: >350° C. (decomp.); IR: KBr ($cm^{-1}$) 2952 (w), 2921(w), 1624(w), 1603(w), 1578(w), 1516(m), 1479(w), 1437(m), 1373(s), 1294(m), 1283(m), 1202(w), 1028(w), 806(m), 754(s), 733(m).

[2,6-Diacetylpyridinebis-(2-methyl-5-(2-methylphenyl)) pyrrol-1-ylimine)]$CoCl_2$ (45):

1.4 g (2.8 mmol) of 2,6-diacetylpyridinebis-(2-methyl-5-(2-methylphenyl))pyrrol-1-ylimine) (26) and 0.36 g (2.8 mmol) of cobalt(II) chloride were stirred at room temperature for 12 hours. The resulting brown precipitate was filtered off and washed a number of times with ether. The part of the complex dissolved in THF was subsequently precipitated completely by means of ether and once again filtered off.

Yield: 0.69 g (1.1 mmol), 39%, $C_{33}H_{33}Cl_2CoN_5$, melting point: >350° C. (decomp.); IR; KBr ($cm^{-1}$) 2921(w), 1626 (m), 1578(m), 1514(m), 1479(w), 1437(w), 1373(s), 1327 (w), 1296(m), 1269(w), 1204(m), 1124(w), 1099(w), 1026 (m), 810(w), 756(s), 733(m), MS: M+−Cl=593 m/e.

[2,6-Diacetylpyridinebis(2-methylindol-1-ylimine)] $FeCl_2$ (46):

0.4 g (0.1 mmol) of 2,6-diacetylpyridinebis(2-methylindol-1-ylimine) (29) dissolved in 100 ml of 2-butanol was slowly added dropwise to a solution of 0.12 g (0.1 mmol) of iron(II) chloride in 50 ml of 2-butanol. After stirring at 40° C. for two hours, the resulting precipitate was filtered off under argon and subsequently digested a number of times with ether.

Yield: 277 mg (0.5 mmol), 53%, $C_{27}H_{25}Cl_2FeN_5$, melting point: >350° C. (decomp.), IR (KBr) $cm^{-1}$: 2917(w), 1609 (m), 1574(m), 1555(w), 1476(w), 1452(s), 1373(s), 1344 (m), 1321(m), 1306(m), 1271(m), 1225(8), 775(m), 742(s).

[2,6-Diacetylpyridinebis-(2-methylindol-1-ylimine)] $CoCl_2$ (47):

0.29 g (0.67 mmol) of 2,6-diacetylpyridinebis(2-methylindol-1-ylimine) (29) and 88 mg (0.67 mmol) of cobalt(II) chloride were dissolved in 50 ml of THF and the mixture was subsequently stirred at room temperature for twelve hours. Complete precipitation with ether, filtration and washing a number of times with ether gives the product in analytically pure form.

Yield: 217 mg (0.40 mmol), 58%, $C_{27}H_{25}Cl_2CoN_5$, melting point: >350° C. (decomp.), IR (KBr) $cm^{-1}$: 3054(w), 2917(w), 1609(m), 1576(m), 1553(w), 1452(s), 1373(s), 1348(s), 1321(s), 1306(m), 1269(m), 1227(m), 1205(w), 1028(w), 1014(w), 812(m), 775(m), 742(s); MS: M+−Cl= 514 m/e.

(2,6-Diacetylpyridinedicarbazol-N-ylimine)$FeCl_2$ (48):

15 ml of 2-butanol were placed in a dry Schlenk tube and flushed with argon for 5 minutes. After addition of 240 mg of 2,6-diacetylpyridinedicarbazol-N-ylimine (30) and 78 mg of iron(II) chloride, the dark brown solution was stirred at 80° C. for two hours. After cooling, the solvent was decanted off and the brown residue was dried in a high vacuum. Yield: 151 mg (49.6%), $C_{33}H_{25}N_5FeCl_2$; Mr: 618.4 g/mol.

(2,6-Diacetylpyridinedicarbazol-N-ylimine)$CoCl_2$ (49):

240 mg of 2,6-diacetylpyridinedicarbazol-N-ylimine (30) and 78 mg of iron(II) chloride were added to 20 ml of absolute tetrahydrofuran. The dark brown solution was stirred at room temperature for 12 hours and the solvent was subsequently taken off in a high vacuum. Yield: 110 mg (87.3%) $C_{33}H_{25}N_5CoCl_2$; Mr: 621.4 g/mol.

[2,6-Diactylpyridinebis(3,5-dimethyl-1,2,4-triazol-4-ylimine)]$FeCl_2$ (50):

250 mg of 2,6-Diacetylpyridinebis(2,5-dimethyl-1,2,4-triazol-4-ylimine) (31) and 450 mg of iron(II) chloride (5 equivalents) were dissolved or suspended in 100 ml of absolute ethanol. The blue solution was stirred at 50° C. for twelve hours and the solvent was then taken off in a high vacuum. Violet residue, 700 mg.

[2,5-Diformylthiophenebis(2,5-diisopropylpyrrol-1-ylimine)]$CoCl_2$ (51):

20 ml of 2-butanol were placed in a dry Schlenk tube and flushed with argon for 5 minutes. After addition of 250 mg of 2,5-diformylthiophenebis(2,5-diisopropylpyrrol-1-ylimine) (32) and 73 mg of cobalt(II) chloride, the dark green solution was stirred at 80° C. for one hour. The solvent was then taken off in a high vacuum and the residue was pulverized. Yield: 285 mg (93.2%) of green powder. $C_{26}H_{36}N_5SCoCl_2$; Mr: 566.5 g/mol.

f) Polymerizations

Polymerization of Ethylene

Standard Polymerization Method 150 ml (or 250 ml) of toluene were placed in a flask which was fitted with a mechanical stirrer and ethylene inlet tube and had been made inert. An amount of a 30% strength solution of methylaluminoxane (MAO) in toluene such that, based on the catalyst complex added later, 100 equivalents were used was then added. For the copolymerizations, 12.5 ml (or 25 ml) of 1-hexene were added. 50 mmol (or 100 mmol) of the complex to be examined were then added thereto. A stream of 40 l/h of ethylene was passed through the reaction solution and the temperature was set to 30° C.

After 1 hour, the reaction was stopped by addition of a mixture of 15 ml of concentrated hydrochloric acid and 50 ml of methanol. If a precipitate was observed, the residue was washed and subsequently dried under slightly subatmospheric pressure. If no precipitate was observed, the phases were separated and the polar phase was shaken with 100 ml of toluene. The organic phases were combined and the volatile constituents were removed under reduced pressure on a rotary evaporator.

Tables 1 and 2 show details of the polymerizations of ethylene using iron (Table 1) and cobalt catalysts (Table 2). Tables 3 and 4 show the analyses of the resulting polyethylene (Table 3: polyethylene obtained by means of iron catalysts, Table 4: polyethylene obtained by means of cobalt catalysts)

TABLE 1

Polymerization of ethylene using iron catalysts

| Polymerization | Catalyst | Batch size [µmol] | Comonomer | Polymer obtained [g] | Activitity[1] [g of PE/mmol of cat.xh] |
|---|---|---|---|---|---|
| C[2]1 | V[3] | 100 |  | 32 | 320 |
| C[2]2 | V[3] | 100 | hexene | 14.5 | 145 |
| 1 | 37 | 100 |  | 19 | 190 |
| 2 | 37 | 50 | hexene | 20.2 | 404 |
| 3 | 34 | 100 |  | 56.5 | 565 |
| 4 | 34 | 100 | hexene | 69 | 690 |
| 5 | 48 | 50 |  | 16 (oil) | 320 |
| 6 | 48 | 50 | hexene | 46 (oil) | 920 |
| 7 | 46 | 50 |  | 16 | 320 |
| 8 | 46 | 50 | hexene | 15.5 | 310 |
| 9 | 42 | 50 |  | 4 | 80 |
| 10 | 42 | 50 | hexene | 49 | 980 |
| 11 | 40 | 50 |  | 3.6 | 72 |
| 12 | 40 | 50 | hexene | 3.7 | 74 |
| 13 | 44 | 50 |  | 1.5 | 30 |
| 14 | 44 | 50 | hexene | 4.8 | 96 |
| 15 | 35 | 50 |  | 1.0 | 20 |

[1]In the case of oils, based on the yield which can be isolated
[2]Comparative experiment
[3]2,6-Diacetylpyridinebis(2,6-dimethylphenylimine)FeCl$_2$

TABLE 2

Polymerization of ethylene using cobalt catalysts

| Polymerization | Catalyst | Batch size [µmol] | Comonomer | Polymer obtained [g] | Activitity[1] [g of PE/mmol of cat.xh] |
|---|---|---|---|---|---|
| 16 | 36 | 100 |  | 1 | 10 |
| 17 | 36 | 100 | hexene | 24 | 240 |
| 18 | 39 | 100 |  | 5 | 50 |
| 19 | 39 | 100 | hexene | 0.6 | 6 |
| 20 | 49 | 50 |  | 2 (oil) | 40 |
| 21 | 49 | 50 | hexene | 2.5 (oil) | 50 |
| 22 | 51 | 50 |  | 0.2 (oil) | 4 |
| 23 | 51 | 50 | hexene | 0.1 (oil) | 2 |
| 24 | 47 | 50 |  | 0.2 | 4 |
| 25 | 47 | 50 | hexene | 0.6 | 12 |
| 26 | 43 | 50 |  | 8.6 | 172 |
| 27 | 43 | 50 | hexene | 11.5 | 230 |
| 28 | 41 | 50 |  | 11.2 (oil) | 224 |
| 29 | 41 | 50 | hexene | 24.2 (oil) | 482 |
| 30 | 45 | 50 |  | 0.6 (oil) | 12 |
| 31 | 45 | 50 | hexene | 1.5 (oil) | 30 |

[1]In the case of oils, based on the yield which can be isolated

TABLE 3

Analyses of the polyethylene (iron catalysts)

| Polymerization | eta value [dl/g] | DSC$_1$ [° C.] | M$_w$[2] | Mn[3] | M$_w$/M$_n$ | Density [g/cm$^3$] |
|---|---|---|---|---|---|---|
| C[4]1 | 2.72 | 135 | 318385 | 7036 | 45 | 0.9596 |
| C[4]2 | 2.71 | 138 | 245448 | 4172 | 59 | 0.9625 |
| 1 | 1.6 | 131 | 112907 | 6483 | 17.4 | 0.9600 |
| 2 | 2.45 | 131 | 205544 | 9298 | 22.1 | 0.9541 |
| 3 | 0.1 | 118 | 3401 | 1273 | 2.7 | 0.9241 |
| 4 | 0.1 | 117 | 3251 | 1440 | 2.3 | 0.9283 |
| 7 | 0.06 | 63 | 1509 | 727 | 2.1 | 0.8913 |
| 8 | 0.12 | 63 | 1477 | 839 | 1.8 | 0.9061 |
| 9 | 0.44 | 120 | 14084 | 1158 | 12.2 | 0.9177 |
| 10 | 0.61 | 121 | 29937 | 1849 | 16.2 | 0.924[5] |
| 11 | 0.22 | 121 | 5438 | 1320 | 4.1 | 0.9338 |
| 12 | 0.21 | 119 | 5956 | 1224 | 4.9 | 0.9317 |
| 13 | 0.31 | 123 | 8183 | 1329 | 6.2 | 0.9387 |
| 14 | 0.18 | 119 | 4737 | 1356 | 3.5 | 0.9387 |
| 15 | 0.1 | 117 | 2281 | 847 | 2.7 |  |

[1]Differential thermal analysis
[2]Weight average molecular weight
[3]Number average molecular weight
[4]Comparative experiment
[5]Hexene content: 2.4 mol %

TABLE 4

Analyses of the polyethylene (cobalt catalysts)

| Polymerization | eta value [dl/g] | DSC$_1$ [° C.] | M$_w$[2] | Mn[3] | M$_w$/M$_n$ | Density [g/cm$^3$] |
|---|---|---|---|---|---|---|
| 16 | 0.1 | 118 | 3582 | 1000 | 3.6 | 0.9271 |
| 17 | 0.05 | 83 | 879 | 659 | 1.3 | 0.9247 |
| 18 | 0.45 | 127 | 13600 | 3181 | 4.3 | 0.9605 |
| 19 | 0.48 | 126 | 9564 | 2735 | 3.5 | 0.9721 |
| 24 | 0.13 | 120 | 5896 | 1478 | 4.0 | 0.9333 |
| 25 | 0.1 | 65 | 1323 | 719 | 1.8 | 0.8948 |
| 26 | 0.27 | 124 | 4985 | 1949 | 2.6 | 0.9563 |
| 27 | 0.17 | 123 | 4565 | 1796 | 2.5 | 0.9528 |

[1]Differential thermal analysis
[2]Weight average molecular weight
[3]Number average molecular weight The polymers from polymerizations 3 and 4 and from polymerizations 5 and 6 were examined in more detail by means of NMR spectroscopy ($^1$H- and $^{13}$C-NMR spectroscopy). Tables 5 and 6 show the data obtained.

TABLE 5

NMR data for the polymers from polymerizations 3 and 4:
Types of branches (in methyl end groups/1000 C)

| Polymerization | Σ Methyl branches[1] | Σ Ethyl branches[1] | Σ Butyl branches[1] | Σ Pentyl branches[1] | Σ > $C_6$ branches[1] | Total Me/10000 $C^2$ |
|---|---|---|---|---|---|---|
| 3 | 3.5 | 0.8 | 0 | 3.4 | 15.9 | 23.6 |
| 4[3] | 6.9 | 1.9 | 9.1 | 6.2 | 26.8 | 50.9 |

[1]Sum of the corresponding branches
[2]Total methyl end groups per 1000 carbon atoms
[3]The sample contains 1.8 mol % of hexene

| | Double bonds/1000 C | |
|---|---|---|
| Polymerization | Vinyl DB[4] | trans DB[4] |
| 3 | 18 | 1.7 |
| 4 | 8.5 | 10.1 |

[4]Number of double bonds per 1000 carbon atoms

TABLE 6

NMR data for the polymers from polymerizations 5 and 6:
Types of branches (in methyl end groups/1000 C)

| Polymerization | Σ Methyl branches[1] | Σ Ethyl branches[1] | Σ Butyl branches[1] | Σ —$C_6$ branches[1] | Total Me/1000 $C^2$ |
|---|---|---|---|---|---|
| 5 | 19 | 71 | 11 | 80 | 181 |
| 6 | 17 | 71 | 15 | 79 | 182 |

[1]Sum of the corresponding branches
[2]Total methyl end groups per 1000 carbon atoms

| | Double bonds/1000 C | | | |
|---|---|---|---|---|
| Polymerization | Vinyl | Vinylidene | cis/trans | CH=C |
| 5 | 1.1 | 0.2 | 4.3 | 0.6 |
| 6 | 1.1 | 0.2 | 4.8 | 0.4 |

Oligomers: Polymerization of ethylene using complex 20

After the polymerization, the reaction solution was worked up using methanol/HCl and the aqueous phase was separated from the toluene phase. A small part of the organic phase was analyzed to determine its composition in an untreated state. The remainder was worked up by removing the solvent under reduced pressure. This gave 2 g of an oil. Both the untreated phase and the oil were analyzed by gas chromatography. Table 7 shows the distribution of carbon chains found.

Weight of toluene solution: 0.3892 g, weight of oil: 0.2467 g

TABLE 7

| Sample | <$C_6$ | $C_6$ | $C_8$ | $C_{10}$ | $C_{12}$ | $C_{14}$ | $C_{16}$ | $C_{18}$ | >$C_{18}$ |
|---|---|---|---|---|---|---|---|---|---|
| Distribution in mg in the sample: | | | | | | | | | |
| Solution | 3 | 7.1 | 9.8 | 7.2 | 4 | 1.9 | 0.9 | 0.4 | 0.4 |
| Oil | | | | | 14.4 | 67.4 | 73.2 | 45.1 | 36.6 |

TABLE 7-continued

| Sample | <$C_6$ | $C_6$ | $C_8$ | $C_{10}$ | $C_{12}$ | $C_{14}$ | $C_{16}$ | $C_{18}$ | >$C_{18}$ |
|---|---|---|---|---|---|---|---|---|---|
| Selectivities in % | | | | | | | | | |
| Solution | 8.6 | 20.5 | 28.5 | 20.7 | 11.5 | 5.5 | 2.6 | 1.2 | 1.2 |
| Oil | | | | | 6.1 | 28.5 | 30.9 | 19 | 15.5 |

It is obvious that the low molecular weight, volatile components were removed together with the solvent in the work-up of the sample. The sample which has not been worked up contains virtually no constituents having more than 18 carbon atoms.

Polymerization of Propene

The polymerization of propene was carried out by a method analogous to the polymerization of ethylene, using propylene instead of ethylene.

Catalyst: Complex 34, batch size: 50 mmol, polymer yield: 15 g (oil), activity (gPE/mmol of catxh): 300.

g) Supported Catalysts:

Preparation of the Support 160 g of silica gel (ES70X, Crosfield) were suspended in 1500 ml of heptane, and 170 ml of a 2 molar solution of trimethylaluminum in heptane were added dropwise over a period of 1 hour. The mixture was stirred for 1 hour and subsequently filtered. The residue was washed with heptane and then dried under reduced pressure.

Loading 119 mg of the complex 34 and 6.8 ml of methylaluminoxane (MAO: 30% strength solution in toluene) were added to a suspension of 10 g of the prepared support in 35 ml of toluene. The mixture was stirred for 30 minutes, filtered, the residue was washed twice with toluene and was subsequently dried under reduced pressure. The catalyst was obtained as a free-flowing powder.

Polymerization

A stirred 1 l steel autoclave was carefully flushed with nitrogen and heated to the polymerization temperature of 70° C., after which 450 ml of isobutane and 60 mg of MAO (as a 30% strength solution in toluene) were introduced. 176 mg of the supported catalyst were then rinsed in using a further 50 ml of isobutane, and the autoclave was then pressurized with to a total pressure of 38 bar. The pressure in the autoclave was kept constant by introduction of further ethylene. After 90 minutes, the polymerization was stopped by venting the autoclave. This gave 120 g of polyethylene; eta Value: 0.6 dl/g.

The figures below show the following:

FIG. 1: 1,4-diketones: 1–7, N-acetamidopyrroles: 8–11, N-aminoheterocycles: 12–21; Me=methyl, i-Pr=isopropyl, Ph=phenyl, o-Tol=ortho-tolyl, R=Me FIG. 2: Ligands: 22–32; Me=methyl, i-Pr=isopropyl, Ph=phenyl, o-Tol=ortho-tolyl FIG. 3: Metal complexes: 34–52; Me=methyl, i-Pr= isopropyl, Ph=phenyl, o-Tol=ortho-tolyl

FIG. 1

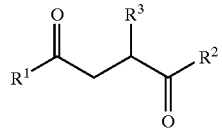

1  $R^1 = R^2 = Me, R^3 = H$
2  $R^1 = R^2 = Me, R^3 = H$
3  $R^1 = Me, R^2 = Ph, R^3 = H$
4  $R^1 = Me, R^2 = i\text{-}Pr, R^3 = H$
5  $R^1 = Me, R^2 = o\text{-}Tol, R^3 = H$
6  $R^1 = R^2 = Me, R^3 = H$
7  $R^1 = R^2 = Me, R^3 = H$

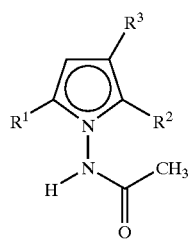

8  $R^1 = Me, R^2 = Me, R^3 = H$
9  $R^1 = Me, R^2 = i\text{-}Pr, R^3 = H$
10 $R^1 = Me, R^2 = o\text{-}Tol, R^3 = H$
11 $R^1 = R^2 = Me, R^3 = H$

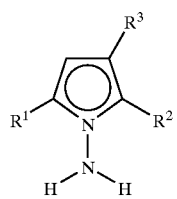

12 $R^1 = R^2 = Me, R^3 = H$
13 $R^1 = R^2 = Me, R^3 = H$
14 $R^1 = Me, R^2 = Ph, R^3 = H$
15 $R^1 = Me, R^2 = i\text{-}Pr, R^3 = H$
16 $R^1 = Me, R^2 = o\text{-}Tol, R^3 = H$
17 $R^1 = R^2 = Me, R^3 = H$
18 $R^1 = R^2 = Me, R^3 = H$

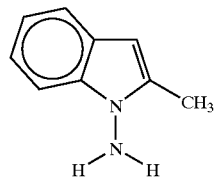

19

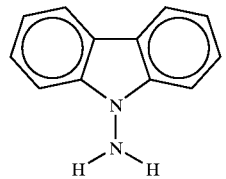

20

-continued

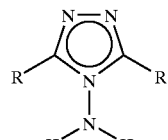

21

FIG. 2

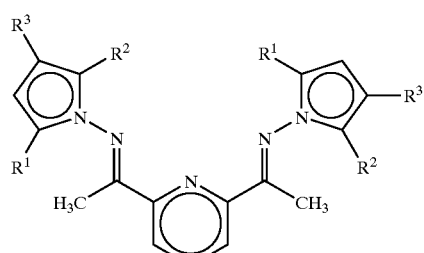

22 $R^1 = R^2 = Me, R^3 = H$
23 $R^1 = R^2 = Me, R^3 = H$
24 $R^1 = Me, R^2 = Ph, R^3 = H$
25 $R^1 = Me, R^2 = i\text{-}Pr, R^3 = H$
26 $R^1 = Me, R^2 = o\text{-}Tol, R^3 = H$
27 $R^1 = R^2 = Me, R^3 = H$
28 $R^1 = R^2 = Me, R^3 = H$

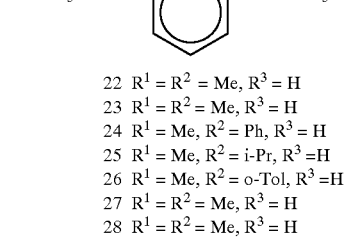

29: R = Me

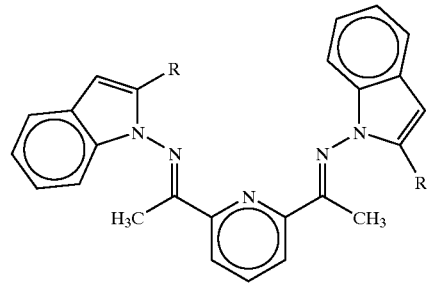

30

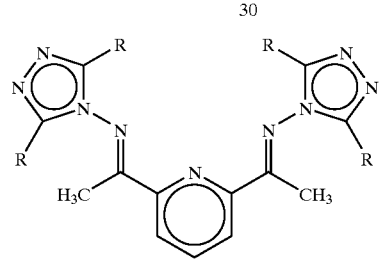

31: R = Me

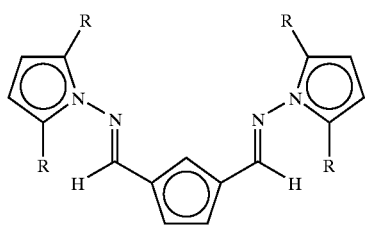

32: R = i-Pr

FIG. 3

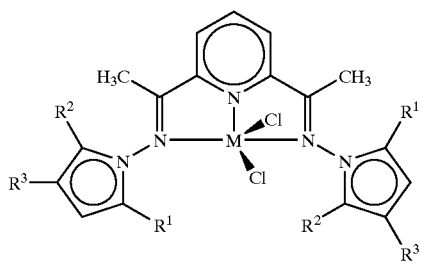

34 R¹ = R² = Me, R³ = H, M = Fe (II)
36 R¹ = R² = Me, R³ = H, M = Co (II)
37 R¹ = R² = i-Pr, R³ = H, M = Fe (II)
39 R¹ = R² = i-Pr, R³ = H, M = Co (II)
40 R¹ = Me, R² = Ph, R³ = H, M = Fe (II)
41 R¹ = Me, R² = Ph, R³ = H, M = Co (II)
42 R¹ = Me, R² = i-Pr, R³ = H, M = Fe (II)
43 R¹ = Me, R² = i-Pr, R³ = H, M = Co (II)
44 R¹ = Me, R² = o-Tol, R³ = H, M = Fe (II)
45 R¹ = Me, R² = o-Tol, R³ = H, M = Co (II)
38 R¹ = R² = Ph, R³ = H, M = Co (II)
39 R¹ = R² = R³ = Ph, M = Co (II)

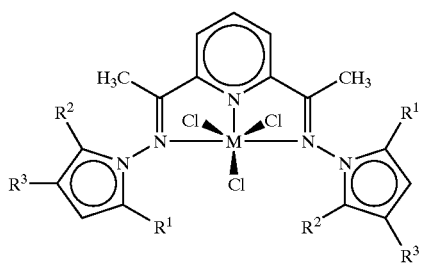

35 R¹ = R² = Me, R³ = H, M = Fe (III)
38 R¹ = R² = i-Pr, R³ = H, M = Fe (III)

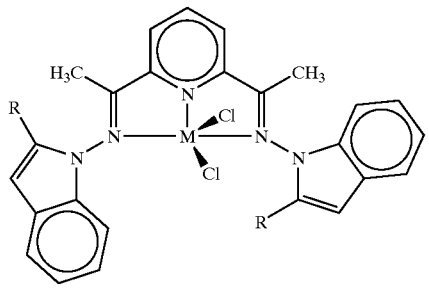

46: R = Me, M = Fe (II)
47: R = Me, M = Co (II)

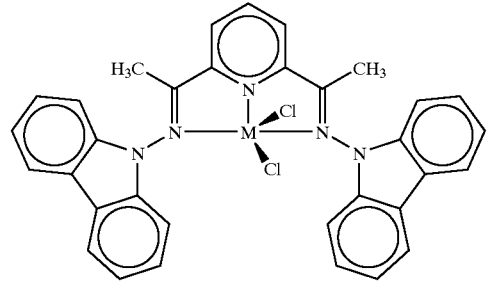

48: M = Fe (II)
49: M = Co (II)

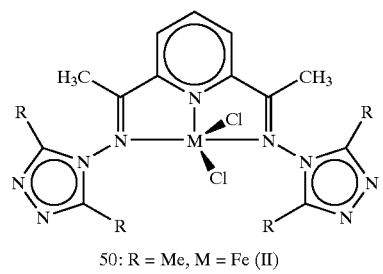

50: R = Me, M = Fe (II)

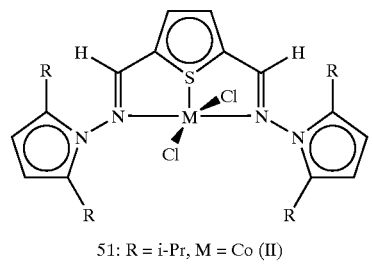

51: R = i-Pr, M = Co (II)

We claim:
1. A compound of the formula (I)

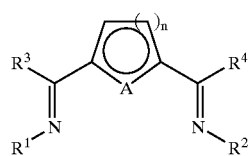

where the symbols have the following meanings:
A is a nonmetal selected from the group consisting of N and P,
$R^1$ is a radical of the formula $NR^5R^6$,
$R^2$ is a radical of the formula $NR^5R^6$ or $NR^7R^8$, alkyl, aryl or cycloalkyl,
$R^5$ and $R^6$ together with the N atom form a pyrrole radical or a radical derived from pyrrole in which one or more —CH— groups in the pyrrole ring may be replaced by nitrogen or which is substituted in the 2 and 5 positions by $C_1$–$C_6$-alkyl groups which may be linear, branched or substituted by heteroatoms, and/or by aryl groups which may be unsubstituted or in turn substituted by heteroatoms or $C_1$–$C_6$-alkyl groups which may be heteroatom-substituted and
$R^7$ and $R^8$ are, independently of one another, alkyl, aryl or cycloalkyl radicals, and
$R^3$, $R^4$ are, independently of one another, H or alkyl, aryl or cycloalkyl radicals, and
n is 1 or 2.

2. A compound as claimed in claim 1, wherein the pyrrole radicals or radicals derived from pyrrole are substituted in the 2 or 5 position by electron-withdrawing radicals selected from the group consisting of halogen,
-trihalomethyl,
$NO_2$, and
sulfonates selected from the group consisting of
$SO_3R'$,
$SO_3SiR'_3$ and
$SO_3$—$(H—NR'_3)^+$, where R' may be identical or different and are selected from the group consisting of H, $C_1$–$C_{10}$-alkyl, $C_6$–$C_{20}$-aryl and $C_5$–$C_8$-cycloalkyl.

3. A compound of the formula (I)

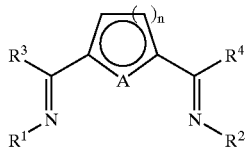

wherein

A is N,
n is 2,
$R^1$ is a radical of the formula $NR^5R^6$,
$R^2$ is a radical of the formula $NR^5R^6$ or $NR^7R^8$, alkyl, aryl or cycloalkyl,
$R^5$ and $R^6$ together with the N atom form a 5-, 6- or 7-membered ring in which one or more of the —CH— or —$CH_2$— groups may be replaced by suitable heteroatom groups and which may be saturated or unsaturated and unsubstituted or substituted or be fused with further carbocyclic or heterocarbocyclic 5 or 6-membered rings which may in turn be saturated or unsaturated and substituted or unsubstituted,
$R^7$ and $R^8$ are, independently of one another, alkyl, aryl or cycloalkyl radicals, and
$R^3$, $R^4$ are, independently of one another, H or alkyl, aryl or cycloalkyl radicals.

4. A compound which corresponds to one of the formulae (Ia), (Ib), (Ic) and (Id):

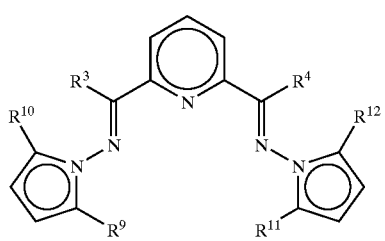
(Ia)

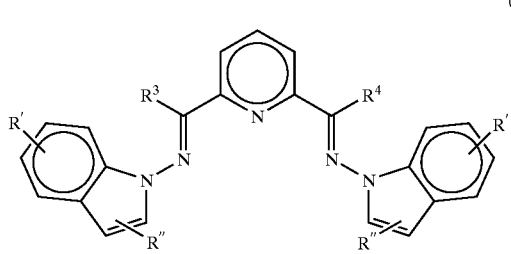
(Ib)

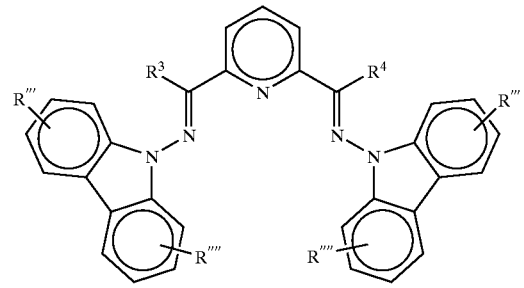
(Ic)

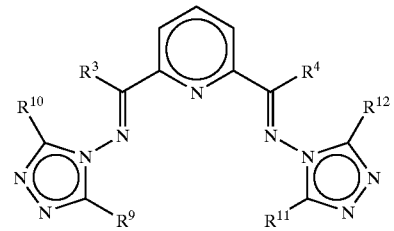
(Id)

where $R^3$, $R^4$ are, independently of one another, H or alkyl or aryl radicals, and
$R^9$, $R^{10}$, $R^{11}$ and $R^{12}$ are, independently of one another, $C_1$–$C_6$-alkyl radicals, and
R', R", R'", R"" are H or alkyl, aryl or cycloalkyl radicals.

5. A process for preparing unsymmetrical compounds of the formula (I)

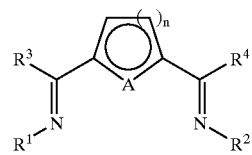

wherein

A is a nonmetal selected from the group consisting of N and P,
n is 1 or 2,
$R^1$ is a radical of the formula $NR^5R^6$,
$R^2$ is a radical of the formula $NR^5R^6$ or $NR^7R^8$, alkyl, aryl or cycloalkyl,
$R^5$ and $R^6$ together with the N atom form a 5-, 6- or 7-membered ring in which one or more of the —CH— or —$CH_2$— groups may be replaced by suitable heteroatom groups and which may be saturated or unsaturated and unsubstituted or substituted or be fused with further carbacyclic or heterocarbacyclic 5- or 6-membered rings which may in turn be saturated or unsaturated and substituted or unsubstituted,
$R^7$ and $R^8$ are, independently of one another, alkyl, aryl or cycloalkyl radicals, and
$R^3$, $R^4$ are, independently of one another, H or alkyl, aryl or cycloalkyl radicals;

in which $R^1 \neq R^2$ in a two-stage process in which a) in a first step, compounds of the formula (II)

$$H_2N—NR^5R^6 \quad (II)$$

are reacted with compounds of the formula (III)

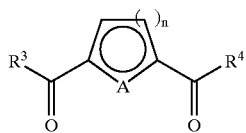

in a mole ratio of the compounds of the formula (II) to the compounds of the formula (III) of 1:0.8–1.2 under acidic conditions in alcoholic solution to form the corresponding monoimine and the solvent is subsequently removed under reduced pressure, and b) the resulting monoimine is, in a second step, reacted with compounds of the formula (II) which differ from the compounds of the formula (II) used in step a); or with compounds of the formula (IV)

or with amines of the formula (V)

where
$R^{13}$ is an alkyl, aryl or cycloalkyl radical, in aprotic solution in the presence of a trialkylaluminum catalyst in a mole ratio of the monoimine to the compound of the formula (II) which differs from the compound of formula (II) used in step a), (IV) or (V) of 1:0.8–1.2.

6. A compound of the formula (I)

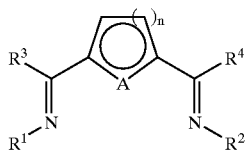

wherein
A is a nonmetal selected from the group consisting of N and P,
n is 1,
$R^1$ is a radical of the formula $NR^5R^6$,
$R^2$ is a radical of the formula $NR^5R^6$ or $NR^7R^8$, alkyl, aryl or cycloalkyl,
$R^5$ and $R^6$ together with the N atom form a 5-, 6- or 7-membered ring in which one or more of the —CH— or —CH$_2$— groups may be replaced by suitable heteroatom groups and which may be saturated or unsaturated an unsubstituted or substituted or be fused with further carbocyclic or heterocarbocyclic 5- or 6-membered rings which may in turn be saturated or unsaturated and substituted or unsubstituted,
$R^7$ and $R^8$ are, independently of one another, alkyl, aryl or cycloalkyl radicals, and
$R^3$, $R^4$ are, independently of one another, H or alkyl, aryl or cycloalkyl radicals;
or wherein
A is P,
n is 1 or 2,
$R^1$ to $R^8$ are as defined above;
or wherein
A is N,
n is 2,
$R^1$ is as defined above,
$R^2$ is a radical of the formula $NR^7R^8$, alkyl, aryl or cycloalkyl,
$R^3$ to $R^8$ are as defined above;
or wherein
A is N,
n is 2,
$R^1$ is as defined above,
$R^2$ is a radical of the formula $NR^5R^6$ or $NR^7R^8$, alkyl, aryl or cycloalkyl,
$R^5$ and $R^6$ together with the N atom form a 6- or 7-membered ring in which one or more of the —CH— or —CH$_2$— groups may be replaced by suitable heteroatom groups and which may be saturated or unsaturated and unsubstituted or substituted or be fused with further carbocyclic or heterocarbocyclic 5- or 6-membered rings which may in turn be saturated or unsaturated and substituted or unsubstituted,
$R^7$ and $R^8$ are as defined above, and
$R^3$, $R^4$ are as defined above;
or wherein
A is N,
n is 1,
$R^1$ is as defined above,
$R^2$ is a radical of the formula $NR^5R^6$ or $NR^7R^8$, alkyl, aryl or cycloalkyl,
$R^5$ and $R^6$ together with the N atom form a 5-membered ring in which none of the other —CH— or —CH$_2$— groups is replaced by a heteroatom group, and which may be saturated or unsaturated and unsubstituted or substituted or be fused with further carbocyclic or heterocarbocyclic 5- or 6-membered rings which may in turn be saturated or unsaturated and substituted or unsubstituted,
$R^7$ and $R^8$ are as defined above, and
$R^3$, $R^4$ are as defined above;
or wherein
A is N,
n is 2,
$R^1$ is as defined above,
$R^2$ is a radical of the formula $NR^5R^6$ or $NR^7R^8$, alkyl, aryl or cycloalkyl,
$R^5$ and $R^6$ together with the N atom form a 5-membered ring in which one or more of the —CH— or —CH$_2$— groups may be replaced by suitable heteroatom groups and which may be saturated or unsaturated and unsubstituted or substituted and is fused with one or more further carbocyclic or heterocarbocyclic 5- or 6-membered rings which may in turn be saturated or unsaturated and substituted or unsubstituted,
$R^7$ and $R^8$ are as defined above, and
$R^3$, $R^4$ are as defined above;
or wherein
A is N,
n is 2,
$R^1$–$R^4$, $R^7$, and $R^8$ are as defined above, and
$R^5$ and $R^6$, together with the N atom form a pyrrole radical which may be substituted or unsubstituted or fused with further carbocyclic 5- or 6-membered rings which may in turn be saturated or unsaturated and substituted or unsubstituted.

7. A process for preparing symmetrical compounds of claim 6 in which $R^1=R^2$ by reacting compounds of the formula (II)

  (II)

where $R^5$ and $R^6$ are as defined in claim 6, with compounds of the formula (III)

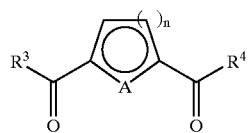  (III)

where $R^3$, $R^4$ are defined as in claim 6,

A is N or P, and n is 1 or 2, in a single-stage process under acidic reaction conditions in alcoholic solution or in the presence of a trialkylaluminum catalyst in an aprotic solvent in a ratio of the compound of the formula (II) to the compound of the formula (III) of 2:0.7–1.3.

* * * * *